US012758139B2

(12) United States Patent
Nanthakumar et al.

(10) Patent No.: US 12,758,139 B2
(45) Date of Patent: Oct. 13, 2026

(54) ELECTRO-ANATOMIC CARDIAC REPOLARIZATION MAPPING

(71) Applicant: University Health Network, Toronto (CA)

(72) Inventors: Kumaraswamy Nanthakumar, Mississauga (CA); Stephane Masse, Toronto (CA); John Asta, King City (CA)

(73) Assignee: University Health Network, Toronto (CA)

( * ) Notice: Subject to any disclaimer, the term of this patent is extended or adjusted under 35 U.S.C. 154(b) by 353 days.

(21) Appl. No.: 18/541,582

(22) Filed: Dec. 15, 2023

(65) Prior Publication Data

US 2024/0197236 A1 Jun. 20, 2024

Related U.S. Application Data

(60) Provisional application No. 63/432,993, filed on Dec. 15, 2022.

(51) Int. Cl.

| | |
|---|---|
| ***A61B 5/367*** | (2021.01) |
| ***A61B 5/308*** | (2021.01) |
| ***A61B 5/341*** | (2021.01) |
| ***A61B 5/366*** | (2021.01) |

(52) U.S. Cl.
CPC .............. *A61B 5/367* (2021.01); *A61B 5/308* (2021.01); *A61B 5/341* (2021.01); *A61B 5/366* (2021.01)

(58) Field of Classification Search
CPC ......... A61B 5/367; A61B 5/308; A61B 5/341; A61B 5/366; A61B 5/7203
See application file for complete search history.

(56) References Cited

U.S. PATENT DOCUMENTS

| | | | | |
|---|---|---|---|---|
| 6,154,672 | A * | 11/2000 | Pendekanti | A61N 1/3956 607/5 |
| 9,248,294 | B2 | 2/2016 | Prinzen et al. | |
| 2004/0082870 | A1* | 4/2004 | Rudy | A61B 5/6852 600/509 |
| 2007/0208265 | A1* | 9/2007 | Couderc | A61B 5/349 600/512 |
| 2007/0265508 | A1* | 11/2007 | Sheikhzadeh-Nadjar | A61B 7/04 607/9 |
| 2018/0125385 | A1* | 5/2018 | Chauhan | A61B 5/366 |
| 2019/0274568 | A1* | 9/2019 | Shahdoostfard | A61B 5/305 |

(Continued)

OTHER PUBLICATIONS

Baas, ECG Based Analysis of Ventricular Respolarisation in the Human Heart, 2012, Karlruhe Transactions on Biomedical Engineering, vol. 18 (Year: 2012).*

(Continued)

*Primary Examiner* — Catherine M Voorhees
(74) *Attorney, Agent, or Firm* — SMART & BIGGAR LP; Tonino Rosario Orsi

(57) ABSTRACT

Various embodiments are described herein for a method for determining at least one repolarization value from Electrogram (EGM) data obtained from a heart using an electrode array, wherein the method comprises: obtaining bipolar EGM data from the EGM data obtained from the heart; determining at least one compound electrogram from the bipolar EGM data; and determining the at least one repolarization value from the at least one compound electrogram.

24 Claims, 15 Drawing Sheets

(56) References Cited

U.S. PATENT DOCUMENTS

2020/0196893 A1* 6/2020 McLeod ................ A61N 1/365
2022/0160307 A1* 5/2022 Zeng ...................... G16H 20/30

OTHER PUBLICATIONS

Auerbach et al., Structural heterogeneity promotes triggered activity, reflection and arrhythmogenesis in cardiomyocyte monolayers. J Physiol. May 1, 2011;589(Pt 9):2363-81.
Baker et al., Enhanced dispersion of repolarization and refractoriness in transgenic mouse hearts promotes reentrant ventricular tachycardia. Circ Res. Mar. 3, 2000;86(4):396-407.
Akar et al., Cellular basis for dispersion of repolarization underlying reentrant arrhythmias. J Electrocardiol. 2000;33 Suppl:23-31.
Chauhan et al. Increased ventricular repolarization heterogeneity in patients with ventricular arrhythmia vulnerability and cardiomyopathy: a human in vivo study. Am J Physiol Heart Circ Physiol. Jan. 2006;290(1):H79-86.
Akar et al., Unique topographical distribution of M cells underlies reentrant mechanism of torsade dr pointes in the long-QT syndrome. Circulation. Mar. 12, 2002;105(10):1247-53.
Banyasz et al., Endocardial versus epicardial differecnes in L-type calcium current in canine ventricular myocytes studied by action potential voltage clamp. Cardiovasc Res. Apr. 1, 2003;58(1):66-75.
Kaufman et al., Influence of heart rate and sympathwetic stimulation on arrhythmogenic T wave alternans. Am J Physiol Heart Circ Physiol. Sep. 2000;279(3):H1248-55.
Kuo et al., Characteristics and possible mechanism of ventricular arrhythmia dependent on the dispersion of action potential durations. Circulations 1983;67:1356-67.
Cowan et al. Sequence of epicardial repolarization and configuration of the T wave. Br Heart J. Nov. 1988;60(5):424-433.
Marrus et al., Repolarization changes underlying long-term cardiac memory due to right ventricular pacing: noninvasive mapping with electrocardiogramaging. Cic Arrhythm Electrophysiol. Aug. 1, 2012;5(4):773-81.
Rivaud et al., Critcal repolarization gradients determine the induction of reentry-based torsades de pointes arrhythmia models of long QT syndrome. Heart Rhythm. Feb. 2021;18(2):278-287.
Haissaguerre et al., Multsite conduction block in the epicardial substrate of Brugada syndrome. Heart Rhythm. Mar. 2022;19(3):417-426.
Behr et al., Brugada syndrome and reduced right ventricular outflow tract conduction reserve: a final common pathway? Eur Heart J. Mar. 14, 2021;42(11):1073-1081.
Nademanee et al., Mechanism of the effects of sodium channel blockade on arrhythmogenic substrate in Brugada syndrome. Heart Rhythm. Mar. 2022;19(3):407-416.
Bhar-Amato et al., Pharmacological Modulation of Right Ventricular Endocardial-Epicardial Gradients in Brugada Syndrome. Circ Arrhythm Electrophysiol. Sep. 2018;11(9):e006330.
Nademanee et al., Fibrosis, Connexin-43, and Conduction Abnormalities in the Bruguda Syndrome. J Am Coll Cardiol. Nov. 3, 2015;66(18):1976-1986.
Szel and Antzelevitch, Abnormal repolarization as the basis for late potentials and fractionated electrograms recorded from epicardium in experimental models of Brugada syndrome. J Am Coll Cardiol. May 20, 2014;63(19):2037-45.
Patocskai et al., Mechanisms Underlying Epicardial Radiofrequency Ablation to Suppress Arrhythmogenesis in Experimental Models of Brugada Syndrome. JACC Clin Electrophysiol. Apr. 2017;3(4):353-363.
Engelman et al., Structural heterogeneity alone is a sufficient substrate for dynamic instability and altered restitution. Circ Arrhythm Electrophysiol. Apr. 2010;3(2):195-203.
Nademanee and Wilde, Repolarization Versus Depolarization Defects in Brugada Syndrome: A Tale of 2 Different Electrophysiologic Settings? JACC Clin Electrophysiol. Apr. 2017;3(4):364-366.
Kubala et al., Analysis of local ventricular repolarization using unipolar recordings in patients with arrhythmogenic right ventricular cardiomyopathy. J Interv Card Electrophysiol. Mar. 2020;57(2):261-270.
Antzelevitch and Fish, Electrical heterogeneity within the ventricular wall. Basic Res Cardiol. 2001;96(6):517-27.
Downar et al., High density intramural mapping of post-infarct premature ventricular contractions and ventricular tachycardia. Pacing Clin Electrophysiol. Oct. 2021;44(10):1781-1785.
Nair et al., Searching for functional M cells in the intact whole human heart: Insights from human langendorff mapping. Canadian Journal of Cardiology. 2011 27(5), S314.
Srinivasan et al. Prolonged action potential duration and dynamic transmural action potential duration heterogeneity underlie vulnerability to ventricular tachycardia in patients undergoing ventricular tachycardia ablation. Europace. 2019;21:616-625.
Peters et al., Reduced content of connexin43 gap junctions in ventricular myocardium from hypertrophied and ischemic human hearts. Circulation 1993;88:864-75.
Srinivasan et al. Dynamic spatial dispersion of repolarization is present in regions critical for ischemic ventricular tachycardia ablation. Heart rhythm O2. 2021;2:280-289.
Millar et al., Correlation between refractory periods and activation-recovery intervals from electrograms: effects of rate and adrenergic interventions. Circulation. 1985:72:1372-1379.
Anter et al., Infarct-Related Ventricular Tachycardia: Redefining the Electrophysiological Substrate of the Isthmus During Sinus Rhythm. JACC Clin Electrophysiol. 2018;4(8):1033-48.
Kelemen et al., Heterogeneous repolarization creates ventricular tachycardia circuits in healed myocardial infarction scar. Nat Commun. 2022;13:830.
Orini et al., Evaluation of the reentry vulnerability index to predict ventricular tachycardia circuits using high-density contact mapping. Hear Rhythm. Apr. 2020;14(4):576-583.
Martin et al., Assessment of a conduction-repolarisation metric to predict Arrhythmogenesis in right ventricular disorders. Int J Cardiol. Nov. 2018;271:75-80.
Juarez et al., Cardiac Repolarization in Health and Disease. JACC. Clinical electrophysiology. 2023;9:124-138 (15 pages).
Kanai and Salama. Optical mapping reveals that repolarization spreads anisotropically and is guided by fiber orientation in guinea pig hearts. Circ Res. Oct. 1995;77(4):784-802.
Joyner, Modulation of repolarization by electrotonic interactions. Jpn Heart J. 1986;27:167-183.
Lesh et al., Cellular uncoupling can unmask dispersion of action potential duration in ventricular myocardium: a computer modelling study. Circ Res. 1989;65:1426-1440.
Graham et al. Simultaneous Comparison of Electrocardiogramaging and Epicardial Contact Mapping in Strucutural Heart Disease. Circ Arrhythm Electrophysiol.Apr. 2019;12(4)e007120.
Ramanathan et al., Noninvasive electrocardiogramaging for cardiac electrophysiology and arrhythmia. Nat Med. Apr. 2004;10(4):422-8.
Lambiase, Rediscovering Repolarization: Timing is Everything. JACC Clin Electrophysiol. Jun. 2022;8(6):719-721.
Massé et al., Electro-anatomic repolarization mapping with orthogonal bipoles and multi-electrode arrays: The next frontier in catheter technology. Heart Rhythm. May 2022;19(5):S9-S10.
Azam et al., Effects of Late Sodium Current Blockade on Ventricular Refibrillation in a Rabbit Model. Circ Arrhythm Electrophysiol. Mar. 2017;10(3):e004331.
Massé et al., Ventricular fibrillation in myopathic human hearts: mechanistic insights from in vivo global endocardial and epicardial mapping. Am J Physiol Heart Circ Physiol. 2007;292:H2589-97.
Callans and Donahue, Repolarization Heterogeneity in Human Post-Infarct Ventricular Tachycardia. J Am Coll Cardiol EP. Jun. 2022, 8(6):713-718.
Yang et al., Spatiotemporal representation of cardiac vectorcardiogram (VCG) signals. BioMedical Engineering OnLine 2012, 11:16 (15 pages).
Rautaharju et al., Usefulness of T-Axis Deviation as an Independent Risk Indicator for Incident Cardiac Events in Older Men and

(56) References Cited

OTHER PUBLICATIONS

Women Free from Coronary Heart Disease (The Cardiovascular Health Study). The American Journal of Cardiology vol. 88 Jul. 15, 2001 (6 pages).
Acar et al., Spatial, temporal and wavefront direction characteristics of 12-lead T-wave morphology. Med. Biol. Eng. Comput., 1999, 37, 574-584 (12 pages).
Child et al., An activation-repolarization time metric to predict localized regions of high susceptibility to reentry. Heart Rhythm 2015;12:1644-1653 (10 pages).
Anderson et al., Wave tail mapping to guide ablation therapy for ventricular arrhythmias. Heart Rhythm. Mar. 2023;20(3):461-470. doi: 10.1016/j.hrthm.2022.10.020. Epub Dec. 16, 2022.
Josephson and Anter, Substrate Mapping for Ventricular Tachycardia—Assumptions and Misconceptions. The American College of Cardiology Foundation (2015) vol. 1, No. 5, ISSN 2405-500X (12 pages).
Chakraborty et al., Effects of azumolene on arrhythmia substrate in a model of recurrent long-duration ventricular fibrillation. Biochemical and Biophysical Research Communications 600 (2022) 123-129 (7 pages).
Deno et al., Orientation-Independent Catheter-Based Characterization of Myocardial Activation. IEEE Transactions on Biomedical Engineering, vol. 64, No. 5, May 2017 (11 pages).
Orini et al., Theoretical Assessment of a Repolarization Time Marker Based on the Intracardiac Bipolar Electrogram. Computing in Cardiology 2017; vol. 44 ISSN: 2325-887X DOI:10.22489/CinC.2017.220-241 (4 pages).
Langfield et al., A novel method to correct repolarization time estimation from unipolar electrograms distorted by standard filtering. Medical image analysis. 2021;72:102075-102075 (11 pages).

* cited by examiner

*Source: *Orini M, Graham AJ, Srinivasan NT, et al. Evaluation of the reentry vulnerability index to predict ventricular tachycardia circuits using high-density contact mapping. Heart Rhythm 2020;14:576–583.*

*Source: *Orini M, Graham AJ, Srinivasan NT, et al. Evaluation of the reentry vulnerability index to predict ventricular tachycardia circuits using high-density contact mapping. Heart Rhythm 2020;14:576–583.*

ELECTRO-ANATOMIC CARDIAC REPOLARIZATION MAPPING

CROSS-REFERENCE TO RELATED APPLICATION

This application claims the benefit of U.S. Provisional Patent Application No. 63/432,993 filed Dec. 15, 2022, which is hereby incorporation by reference in its entirety.

FIELD

Various embodiments are described herein that generally relate to methods and systems for determining electro-anatomic repolarization.

BACKGROUND

The following paragraphs are provided by way of background to the present disclosure. They are not, however, an admission that anything discussed therein is prior art or part of the knowledge of persons skilled in the art.

The mainstay of antiarrhythmic pharmacological treatments has been to lengthen repolarization, homogenize repolarization and modify the excitable gap. Pharmacological strategies of Class 1 and 3 antiarrhythmic drugs utilize global therapeutic effects and is limited, as targeting specific ion channels in pro-arrhythmic sites has not been possible leading to unwanted effects. Catheter-based therapies have mainly concentrated on depolarization and wavefront mapping, in particular the delay in activation, allowing treatment to selected regions of disease or arrhythmogenicity. Cardiac mapping for VT therapy has focused on activation or wavefront mapping during VT. Other wavefront mapping such as substrate-based approaches during sinus or paced rhythm has been the historically preferred tool for localizing VT ablation targets. Techniques have been developed to locate prepotentials, Purkinje potentials, late activation as well as substrate methods such as local abnormal ventricular activity (LAVA) and decrement evoked potential (DeEP) mapping. All of these approaches rely on the depolarization or wave front with no consideration of wave tail or local tissue repolarization.

Compared to depolarization and wavefront that spreads fast, cardiac repolarization and wave tail is temporally dispersed over a longer time: by a factor of at least 10-fold and heightened in the diseased myocardium. In fact, slow conduction or conduction block in diseased myocardium is largely driven by prolonged repolarization and calcium-dependent conduction, wavefront wave tail interactions rather than reduced excitability alone.[1] Yet, clinical substrate mapping relies heavily on measuring depolarization and wavefront rather than the underlying primary wavefront wave tail interactions. Potassium channel distribution heterogeneity is much greater than sodium channel heterogeneity in surviving myocardial tissue that supports ventricular tachycardia in cardiomyopathy. Direct measures of repolarization differences may be therefore more reflective of primary disease than measuring local conduction delays. Heterogeneity in repolarization is more prevalent than depolarization and is a known greater driver of arrhythmogenicity.[2,3] Therefore, diseased myocardial tissue is more likely to manifest and be detectable during repolarization and behavior of the wave tail. There is emerging data to show targeting repolarization has mechanistically a more profound anti-arrhythmic impact.

It has clearly been established that repolarization heterogeneity and gradients are risk markers in VT/VF.[4] As several ion channels are responsible for repolarization ($K^+$ channel types such as $I_{Ks}$, $I_{Kr}$, calcium channels such as $I_{Ca-T}$, $I_{Ca-L}$ and $I_{to}$)[5,6] in contrast to depolarization (sodium channels), it is possible that repolarization abnormalities are more vulnerable to disease and may precede any manifestation of conduction delay. This infers that assessment may allow early diagnosis of at-risk patients. Also, repolarization metrics are more susceptible to changes in the rate of activation, and as described by Rosenbaum,[7] T wave alternans (TWA) precedes QRS alternans with increasing heart rate.

In addition, steep gradients of repolarization are known to be a predisposing factor for VAs. Repolarization gradients correlate with disease severity.[8] It has previously been shown that in patients with upright T waves, the repolarization sequence is predominantly determined by the activation sequence.[9] Consequently, this inverse relationship between the duration of the action potential and activation time reduces the dispersion of repolarization, which may be protective against VA development. In contrast, patients with an inverted T wave, the action potential is independent of the activation time and dispersion of repolarization is increased.[9]

Using ECG-I, epicardial spatial gradients in repolarization applying the inverse solution to unipoles have been observed in a variety of primary electrical disorders such as Long QT, Brugada and Early repolarization syndromes as well as pacemaker-induced cardiac memory.[10] Additionally, recent seminal work by Rivaud and Coronel[11] convincingly demonstrated sustained VT pivots around lines of repolarization gradients opening the door now for catheter-based therapy targeting cardiac repolarization abnormalities. Thus, repolarization gradient mapping may be of relevance in delineating VT/VF substrate in ischemic, nonischemic cardiomyopathy and channelopathies where arrhythmia is often pleomorphic and there is otherwise paucity of fixed conduction corridors, depolarization abnormalities and late potentials are sparse in the endocardium. Epicardial or intramural sites may also be better deciphered as inherently low frequency changes may be detectable from the epicardium.

Evidence supporting repolarization as an arrhythmia substrate and ablation target in various disease states has been serendipitously accumulating and is the original motivation for this viewpoint. The literature supports a variety of disease states where repolarization has been targeted for catheter-based therapy. Repolarization ablation targets have been used in Brugada, Early repolarization, ARVC and, more recently, ischemic cardiomyopathy.

For example, the underlying electrophysiologic basis of Brugada syndrome (BrS) is still highly controversial as to being primarily an example of the concept of repolarization dispersion (repolarization hypothesis) or due to abnormal myocardial structure and conduction abnormalities (depolarization hypothesis), or a combination of both mechanisms. Increased epicardial and interstitial fibrosis and RVOT endomyocardial biopsy evidence of fibrosis in the setting of a genetic variation and sodium channel blockade explain fragmented electrograms, excitation failure, delayed depolarization, reduced gap junction expression and short-coupled PVCs as the cause of ventricular arrhythmias and the typical BrS ECG pattern in V1-V3.[12-14] It is also possible that repolarization gradients develop transmurally most likely due to cellular uncoupling due to fibrosis which promotes electrotonic uncoupling.[15,16] Phase II re-entry across the myocardial wall due to heterogenous loss of transient outward potassium current Ito-mediated epicardial action potential (AP) dome exaggerates differential repolarization currents between the epicardium and endocardium resulting in formation of gradients during both phase I and II of the AP facilitating the development of VAs. Szel and Antzelevitch[17] as well as Patocskai and Antzelevitch[18] provided a compelling alternative explanation for the epicardial substrate abnormalities in BrS described by Nadamanee[16], directly linking these as a consequence of repolarization, not depolarization. Using Pinacidil and ajmaline, two BrS models to mimic either gain of function of the $I_{to}$ or $I_{K\text{-}ATP}$ channels and loss of function of the $I_{Ca}$ and $I_{Na}$ channels, respectively, arrhythmogenic substrate was mapped from drug-infused RV tissue samples until PVCs, polymorphic VT and VF induced. Dynamic, low voltage fractionated bipolar electrograms (EGMs) were generated in the presence of accentuated epicardial AP 'spike-and-dome' appearance and late potentials as a result of concealed phase 2 re-entry. Furthermore, bipolar EGM abnormalities may be reversed with normalization of the epicardial AP second upstroke. These findings strongly support that fractionation of the epicardial EGMs are secondary to heightened AP notching and concealed phase 2 re-entry and not due to conduction slowing. Finally, abolishment of the repolarization pattern rendering patients VT-free suggests that regions of repolarization abnormality may be potential targets for radiofrequency-based therapy. Presumably, ablation normalizes BrS patterns by removing the 'critical substrate' myocytes with accentuated AP notching and overall reducing the Ito concentration and hence eliminating the repolarization gradient. This also suggests that the targets identified by Nadamanee and Pappone are not only related to the repolarization duration gradient, but the phase and shape of AP are also important to examine within the substrate for ablation. Repolarization gradients can also occur between neighboring endocardial or epicardial surfaces and is also possible for the gradients to occur transmurally involving epicardial, mid-myocardial and endocardial surfaces. It must be reiterated that evidence for a repolarization abnormality is derived solely from wedge preparation and computational models[19], clinical data in BrS patients convincingly demonstrating RVOT transmural gradients in human BrS is lacking.[20]

In long Qt, QT prolonging therapies and primary mutations in channels mediating repolarization currents underpin the electrophysiological basis of R from T complexes, Torsades de pointes (TdP) and subsequent polymorphic VT in long QT syndromes. Recently, Rivaud and Coronel[11] demonstrated in a sotalol-infused porcine Langendorff model, that TdP initiation was dependent on RT heterogeneity where the critical difference between the short RT and long RT was if this interval exceeded 69 ms. Furthermore, the duration of the short RT could not exceed 331 ms to trigger TdP. Following initiation, phase singularities were maintained by figure-of-8 re-entry anchored by a core functional line of block wandering along sites of repolarization gradients (border of short and long repolarization regions) depicted as double potentials. These findings support the notion that localization of repolarization gradients in long QT and other arrhythmogenic syndromes is a potential target of substrate modification with catheter ablation, even in substrate devoid of conventional bipolar substrate abnormalities.

In Arrhythmogenic right ventricular cardiomyopathy, repolarization abnormalities may complement depolarization findings in ARVC most exemplified by T wave inversion on ECG leads V1-V3, or may be used to identify early disease when typical arrhythmogenic regions of slow conduction are sparse. The role of repolarization mapping as an adjunct to depolarization mapping is emerging. The genesis of T wave inversion in ARVC involves amplified AP gradients between the endocardium and epicardium leading to local spatial dispersion of repolarization. Detailed mapping was performed in 21 ARVC patients with analysis of the unipolar EGM repolarization parameters including the morphology and negative amplitude of the T wave, Q-Tpeak interval and Tpeak-Tend intervals.[21] Tpeak has been shown in experimental models to correspond to full repolarization.[22] Epicardial negative T wave area was significantly larger than healthy controls and these regions correlated strongly to typical abnormal substrate including critical VT sites as determined by activation and entrainment.

In Ischemic and non-ischemic cardiomyopathies, repolarization mapping as an ablation target in ischemic or cardiomyopathic hearts is an attractive mechanistic strategy. The utility of high-density, simultaneous unipolar EGM mapping in an early ischemia model has been shown to define the mechanism of spontaneous PVCs being linked to transmural re-entry.[23] Studies have shown that LV remodeling in failing human myocardium results in prolongation of the action potential duration (APD) and refractory periods, APD alternans and heterogeneous prolongation of APD. In humans, intramural repolarization gradients have not previously been evaluated due to the obvious limitation of instrumentation of this region and interpretation of low frequency content signatures of repolarization. Furthermore, cut sections of human heart with optical mapping to identify M cells have not been able to prove this concept. We have previously evaluated M cells using an intact human heart model with multiple plunge needles and not identified M cells.[24] This may be due to the fact that these cells are electrotonically coupled in intact human hearts and hence their electrophysiological properties cannot be distinguished.

In healthy human heart, repolarization in the epicardium is on a different time course compared to the endocardium. Both endocardial and epicardial activation recovery interval (ARI) get locally prolonged in border zone and dense scar irrespective of scar location, with greater proportional lengthening of ARI in the epicardium than endocardium.[25] This minimizes the transmural dispersion of repolarization in scarred regions, possibly to compensate for further reduction in conduction velocity in the epicardium from greater proportional downregulation of Cx43 in the epicardium.[26] When opposing endocardial and epicardial scar patterns are congruent, the transmural dispersion of repolarization appears to diminish. Some degree of transmural dispersion of repolarization is preserved when either endocardial or epicardial scar is opposite normal paced tissue.

In models of healed ischemic scar with VT, ARI is prolonged and there is dynamic spatial dispersion of repolarization in critical isthmus sites. Srinivasan and colleagues[27] used the Wyatt method to automate repolarization time color maps. The repolarization time (RT) was defined as activation time maximum negative dV/dt to the upslope of the unipolar EGM T wave (whether negative or positive). An additional "dynamic" protocol was added to sinus rhythm substrate-based mapping with a single sensed extra-stimulus from the RV apex. Maps were created in 20 patients and compared to isthmus sites as defined by activation/entrainment (70%) or pacemap mapping. RT was most prolonged in dense scar (voltage <0.5 mV), progressively shortening in border zone scar and normal voltage. RT was further exaggerated when only utilizing the single extra-stimulus maps where it was most prolonged in dense scar. Furthermore, RT was significantly longer in regions of LPs, and, again amplified by the extra-stimulus protocol. Spatial dispersion of repolarization was significantly prolonged in critical isthmus sites when stressing the substrate with the extra-stimulus protocol. Importantly, in that study no difference in repolarization was seen in critical sites when mapping only in sinus rhythm. These data promote the concept that critical isthmus sites harbor the cellular constituents for heterogenous dynamic refractory properties and low-voltage corridors susceptible to unidirectional block facilitating reentry.

Callans and Donahue[28] described repolarization heterogeneity in human post-infarct VT with significantly shorter ARIs in isthmus-proven sites, supporting experimental studies demonstrating spatial dispersion of refractoriness in non-infarct conditions. In 6 patients undergoing clinically-indicated VT ablation, critical circuit sites were demonstrated with gold standard entrainment or pacemap matching with a long stimulus-to-QRS using point-by-point mapping. Unipolar EGMs were bandpass filtered at 2 to 240 Hz, ARI as a surrogate of local action potential duration[29] was measured from maximum negative dV/dt of activation to the either the upslope or downslope for negative and positive T waves, respectively. As previously demonstrated,[30] traditional bipolar EGM abnormalities including duration, fractionation, split and late potentials lacked specificity as they were equally found in non-isthmus sites. However, ARI was significantly shorter in isthmus sites compared to adjacent non-isthmus sites (420.2 ms vs 462.5 ms). Impressively, ARI was found to be shortest in 3 of 4 patients with first-ablation lesion VT termination. Possible mechanistic explanations of these findings may relate to earlier porcine work showing remodeling-associated upregulation of $I_{Ks}$ channels shortened APD was specific to the isthmus.[31] Furthermore, genetic transfer of a non-functional potassium channel gene prevented VT, providing validation that normalizing repolarization gradients and the role of gene therapy may be a therapeutic target.

SUMMARY OF VARIOUS EMBODIMENTS

In accordance with one aspect of the teachings herein, there is provided a method for determining at least one repolarization value from Electrogram (EGM) data obtained from a heart using an electrode array, wherein the method is performed by at least one processor and/or circuitry wherein the method comprises: obtaining bipolar EGM data from the EGM data obtained from the heart; determining at least one compound electrogram from the bipolar EGM data; and determining the at least one repolarization value from the at least one compound electrogram.

In at least one embodiment, the method further comprises filtering the EGM data by performing high pass filtering using a cutoff frequency of about 0.02 Hz or about 0.05 Hz.

In at least one embodiment, the method comprises preprocessing the obtained EGM data by performing baseline correction.

In at least one embodiment, the method includes preprocessing the obtained EGM data by performing noise reduction.

In at least one embodiment, the method comprises obtaining the bipolar EGM data by applying differential amplification when obtaining the EGM data from the heart.

In at least one embodiment, the method comprises obtaining the bipolar EGM data from a principal component referenced unipole or is an EGM derived from a Laplacian operation.

In at least one embodiment, the method comprises obtaining the bipolar EGM data by subtracting EGM data for a first electrode from EGM data for a second electrode where the first and second electrodes are adjacent to one another in the electrode array.

In at least one embodiment, the at least one compound electrogram is an orthogonal bipolar compound electrogram.

In at least one embodiment, a given orthogonal bipolar compound electrogram is obtained by: obtaining an Along Bipolar EGM for a first pair of electrodes disposed adjacent to one another and along a linear array of electrodes from the electrode array; obtaining an Across Bipolar EGM for a second pair of electrodes that are orthogonal to the first pair of electrodes and share a common electrode therewith; and combining the Along Bipolar EGM and the Across Bipolar EGM in an orthogonal manner to obtain the orthogonal bipolar compound electrogram.

In at least one embodiment, combining the Along Bipolar EGM and the Across Bipolar EGM comprises squaring the Along Bipolar EGM, squaring the Across Bipolar EGM and adding the squared Along Bipolar EGM and squared Across Bipolar EGM.

In at least one embodiment, a repolarization value for a given orthogonal bipolar compound electrogram is obtained by: determining a local activation time; determining a fiducial time point based on an intersection of a first line that is aligned with a diastolic baseline and a second that is aligned with a most negative slope of a portion of the orthogonal bipolar compound EGM; and obtaining the repolarization value from a repolarization time defined by a time duration between the local activation time and the fiducial time point.

In at least one embodiment, the at least one compound electrogram is a loop vector compound electrogram.

In at least one embodiment, a given loop vector compound electrogram is obtained by: selecting an orthogonal set of electrodes where horizontally adjacent electrodes are on separate linear electrode arrays and vertically horizontal adjacent electrodes are on a same linear electrode array; forming an orthogonal set of bipoles using the selected orthogonal set of electrodes; deriving a vectorcardiogram-like loop from the orthogonal set of bipoles; identifying a T loop portion from the vectorcardiogram-like loop; and obtaining a derivative of the vectorcardiogram by obtaining a time projection of the repolarization loop along a maximum axis of the T loop portion thereby forming the loop vector compound electrogram.

In at least one embodiment, the repolarization value for a given loop vector compound electrogram is obtained by: determining a first time point that is an onset of a QRS complex in the loop vector compound electrogram; determining a second time point that is a baseline return of the loop vector compound electrogram; and obtaining the repolarization value from a repolarization time defined by a time duration between the first time point and the second time point.

In at least one embodiment, the method comprises obtaining a plurality of repolarization values corresponding to various locations on an electrode grid defined by the electrode array.

In at least one embodiment, the method further comprises determining a plurality of repolarization values for generating a repolarization map that is displayed on a display, stored in a data store, transmitted to another computing device or any combination thereof.

In at least one embodiment, the repolarization map is used to guide a cardiac procedure including catheter ablation and/or tissue debulking.

In another aspect, in accordance with the teachings herein, there is provided a system for determining at least one repolarization value from Electrogram (EGM) data obtained from a heart, wherein the system comprises: an electrode array for obtaining EGM data from the heart; an instrumentation unit that is coupled to the electrode array and is configured to receive and preprocess the obtained EGM data; memory for storing program instructions; and at least one processor that is coupled to the memory and the instrumentation unit, wherein when the at least one processor executes the program instructions, the at least one processor is configured to perform a method that is defined according to any one of the embodiments described herein.

In at least one embodiment, the instrument unit comprises at least one filter for filtering the EGM data by performing high pass filtering using a cutoff frequency of about 0.02 Hz or about 0.05 Hz.

In at least one embodiment, the instrumentation unit comprises circuitry that is configured and/or the at least one processor is configured for preprocessing the obtained EGM data by performing baseline correction.

In at least one embodiment, the circuitry of the instrumentation unit is configured and/or the at least one processor is configured to preprocess the obtained EGM data by performing noise reduction.

In at least one embodiment, the instrumentation unit comprises at least one differential amplifier for obtaining the bipolar EGM data by applying differential amplification when obtaining the EGM data from the heart.

In at least one embodiment, the at least one processor is configured to obtain the bipolar EGM data from a principal component referenced unipole or is an EGM derived from a Laplacian operation.

In at least one embodiment, the at least one processor or the instrumentation unit is configured to obtain the bipolar EGM data by subtracting EGM data for a first electrode from EGM data for a second electrode where the first and second electrodes are adjacent to one another in the electrode array.

In at least one embodiment, the at least one processor is configured to obtain a given orthogonal bipolar compound electrogram by: obtaining an Along Bipolar EGM for a first pair of electrodes disposed adjacent to one another and along a linear array of electrodes from the electrode array; obtaining an Across Bipolar EGM for a second pair of electrodes that are orthogonal to the first pair of electrodes and share a common electrode therewith; and combining the Along Bipolar EGM and the Across Bipolar EGM in an orthogonal manner to obtain the orthogonal bipolar compound electrogram.

In at least one embodiment, the at least one processor is configured to combine the Along Bipolar EGM and the Across Bipolar EGM comprises squaring the Along Bipolar EGM, squaring the Across Bipolar EGM and adding the squared Along Bipolar EGM and squared Across Bipolar EGM.

In at least one embodiment, the at least one processor is configured to obtain a repolarization value for a given orthogonal bipolar compound electrogram by: determining a local activation time; determining a fiducial time point based on an intersection of a first line that is aligned with a diastolic baseline and a second that is aligned with a most negative slope of a portion of the orthogonal bipolar compound EGM; and obtaining the repolarization value from a repolarization time defined by a time duration between the local activation time and the fiducial time point.

In at least one embodiment, the at least one processor is configured to obtain a given loop vector compound electrogram by: selecting an orthogonal set of electrodes where horizontally adjacent electrodes are on separate linear electrode arrays and vertically horizontal adjacent electrodes are on a same linear electrode array; forming an orthogonal set of bipoles using the selected orthogonal set of electrodes; deriving a vectorcardiogram-like loop from the orthogonal set of bipoles; identifying a T loop portion from the vectorcardiogram-like loop; and obtaining a derivative of the vectorcardiogram by obtaining a time projection of the repolarization loop along a maximum axis of the T loop portion thereby forming the loop vector compound electrogram.

In at least one embodiment, the at least one processor is configured to obtain a repolarization value for a given loop vector compound electrogram by: determining a first time point that is an onset of a QRS complex in the loop vector compound electrogram; determining a second time point that is a baseline return of the loop vector compound electrogram; and obtaining the repolarization value from a repolarization time defined by a time duration between the first time point and the second time point.

In at least one embodiment, the at least one processor is configured to obtain a plurality of repolarization values corresponding to various locations on an electrode grid defined by the electrode array.

In at least one embodiment, the at least one processor is configured to determine a plurality of repolarization values for generating a repolarization map that is displayed on a display, stored in a data store, transmitted to another computing device or any combination thereof.

In another aspect, in accordance with the teachings herein, there is provided a non-transitory computer readable medium storing program instructions that when executed by a processor cause the processor to perform a method for determining at least one repolarization value where the method that is defined according to any one of the embodiments described herein.

Other features and advantages of the present application will become apparent from the following detailed description taken together with the accompanying drawings. It should be understood, however, that the detailed description and the specific examples, while indicating preferred embodiments of the application, are given by way of illustration only, since changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIGS. 3A-3E show examples of reentry vulnerability index (RVI) identifying vulnerable sites close to an entrained ventricular tachycardia (VT) (source for FIGS. 3A-3E: Orini M, Graham A J, Srinivasan N T, et al. *Evaluation of the reentry vulnerability index to predict ventricular tachycardia circuits using high-density contact mapping. Heart Rhythm* 2020; 14:576-583.).

Figure 1A:
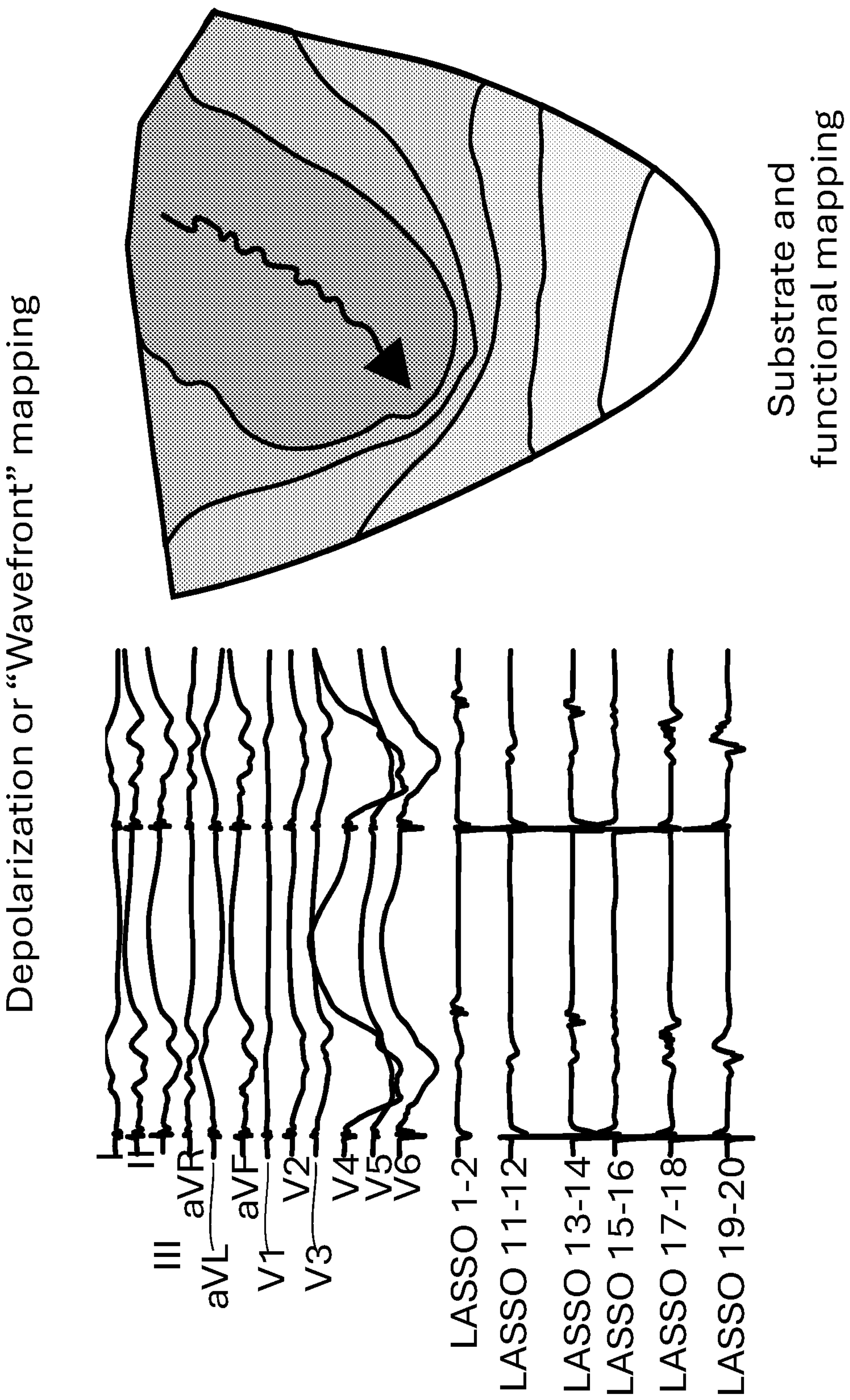
FIG. 1A (Prior Art)
FIG. 1A shows an overview of traditional depolarization or "wavefront" mapping techniques including substrate and activation or entrainment mapping.
Figure 1A:
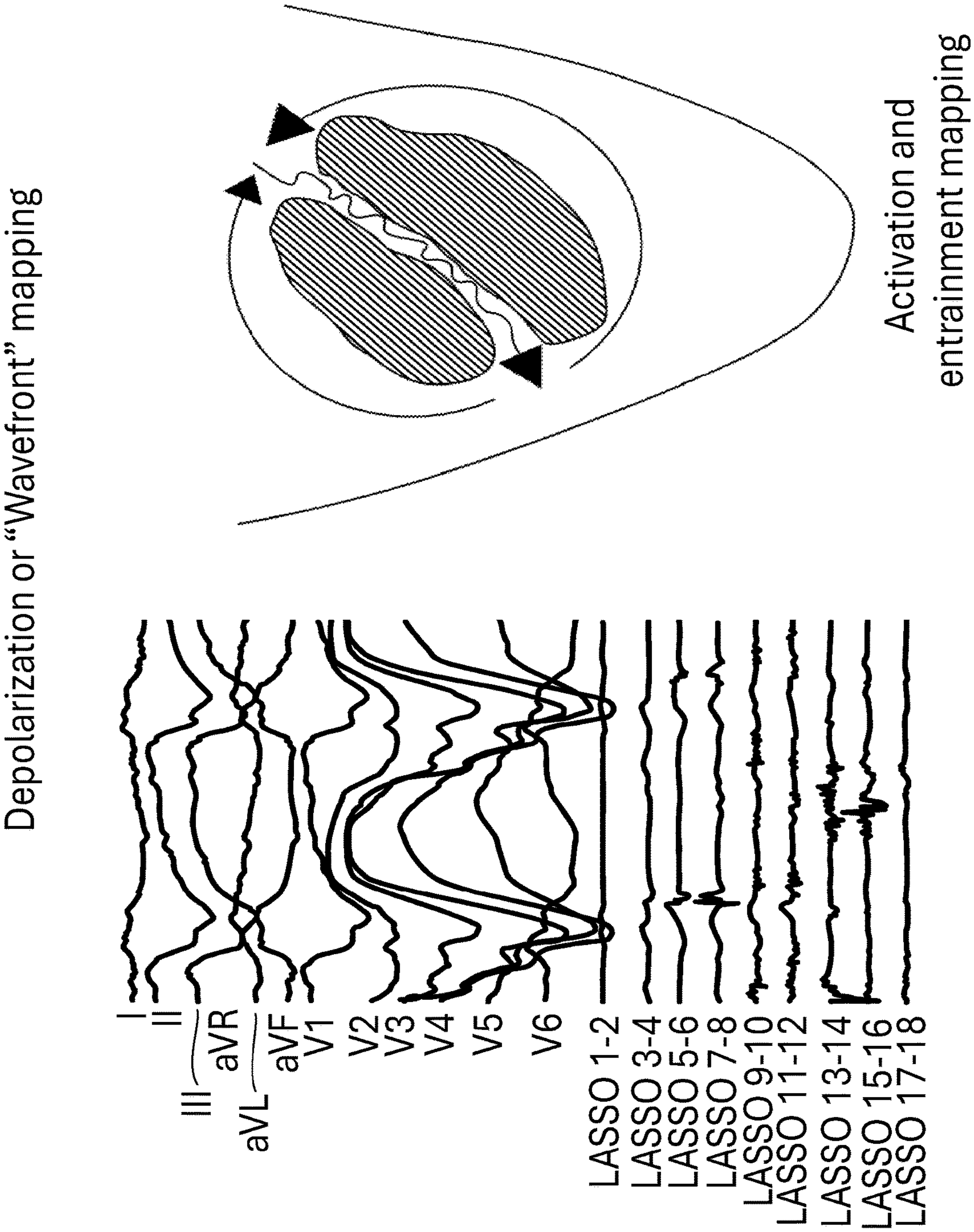
FIG. 1A (cont'd) (Prior Art)

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices, systems or methods having all of the features of any one of the devices, systems or methods described below or to features common to multiple or all of the devices, systems or methods described herein. It is possible that there may be a device, system or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled", or "coupling" as used herein can have several different meanings depending in the context in which these terms are used. For example, the terms coupled, or coupling can have a mechanical, electrical or fluidic connotation. For example, as used herein, the terms coupled or coupling can indicate that two elements or devices can be directly connected to one another or connected to one another through one or more intermediate elements or devices via an electrical signal, electrical connection, fluidic pathway or a mechanical element depending on the particular context.

Unless the context requires otherwise, throughout the specification and claims which follow, the word "comprise" and variations thereof, such as, "comprises" and "comprising" are to be construed in an open, inclusive sense, that is, as "including, but not limited to".

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any operable combination thereof. Accordingly, the term "any combination thereof" is meant to cover any operable combination of the elements which precede the phrase. For example, the phrase "A, B, C, D or any combination thereof" includes A; B; C; D; A and B; A and C; A and D; B and C; B and D; C and D; A, B and C; A, B and D; A, C and D; B, C and D as well as A, B, C and D assuming that all such combinations are operable (i.e., they can be used together in practice in a working embodiment).

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5% or 10%, for example, if this deviation does not negate the meaning of the term it modifies.

Furthermore, the recitation of numerical ranges by endpoints herein includes all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or 10%, for example.

Reference throughout this specification to "one embodiment", "an embodiment", "at least one embodiment" or "some embodiments" means that one or more particular features, structures, or characteristics may be combined in any suitable operable manner in one or more embodiments, unless otherwise specified to be not combinable or to be alternative options.

As used in this specification and the appended claims, the singular forms "a," "an," and "the" include plural referents unless the content clearly dictates otherwise. It should also be noted that the term "or" is generally employed in its broadest sense, that is, as meaning "and/or" unless the content clearly dictates otherwise.

Throughout this specification and the appended claims, infinitive verb forms are often used. Examples include, without limitation: "to detect," "to provide," "to transmit," "to communicate," "to process," "to route," and the like. Unless the specific context requires otherwise, such infinitive verb forms are used in an open, inclusive sense, that is as "to, at least, detect" "to, at least, provide," "to, at least, transmit," and so on.

A portion of the example embodiments of the systems, devices, or methods described in accordance with the teachings herein may be implemented as a combination of hardware and/or software. For example, a portion of the embodiments described herein may be implemented, at least in part, by using one or more computer programs, executing on one or more programmable devices comprising at least one processing element, and at least one data storage element (including volatile and non-volatile memory). These devices may also have at least one input device (e.g., a keyboard, a mouse, a touchscreen, other input elements or any operable combination thereof) and at least one output device (e.g., a display screen, a printer, a wireless radio, other output elements or any operable combination thereof) depending on the type of device.

It should also be noted that there may be some elements that are used to implement at least part of the embodiments described herein that may be implemented via software that is written in a high-level procedural language such as object-oriented programming. The program code may be written in C, $C^{++}$ or any other suitable programming language and may comprise modules or classes, as is known to those skilled in object-oriented programming. Alternatively, or in addition thereto, some of these elements implemented via software may be written in assembly language, machine language, or firmware as needed.

At least some of the software programs used to implement at least one of the embodiments described herein may be stored on a storage media or a device that is readable by a general or special purpose programmable device. The software program code, when read by the programmable device, configures the programmable device to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions, such as program code, for one or more processors. The program code may be preinstalled and embedded during manufacture and/or may be later installed as an update for an already deployed computing system. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g., downloads), media, digital and analog signals, and the like. The computer useable instructions may also be in various formats, including compiled and non-compiled code.

Accordingly, any device described herein that executes software instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information, and which can be accessed by an application, module, or both. Any such computer storage media may be part of the device or accessible or connectable thereto.

It should also be noted that the terms bipole and bipolar may be used interchangeably herein to mean the same thing. In addition, the terms Bipole EGM and Bipolar EGM may be used interchangeably herein to mean the same thing. Furthermore, the terms unipole and unipolar may be used interchangeably herein to mean the same thing.

Figure 1B:
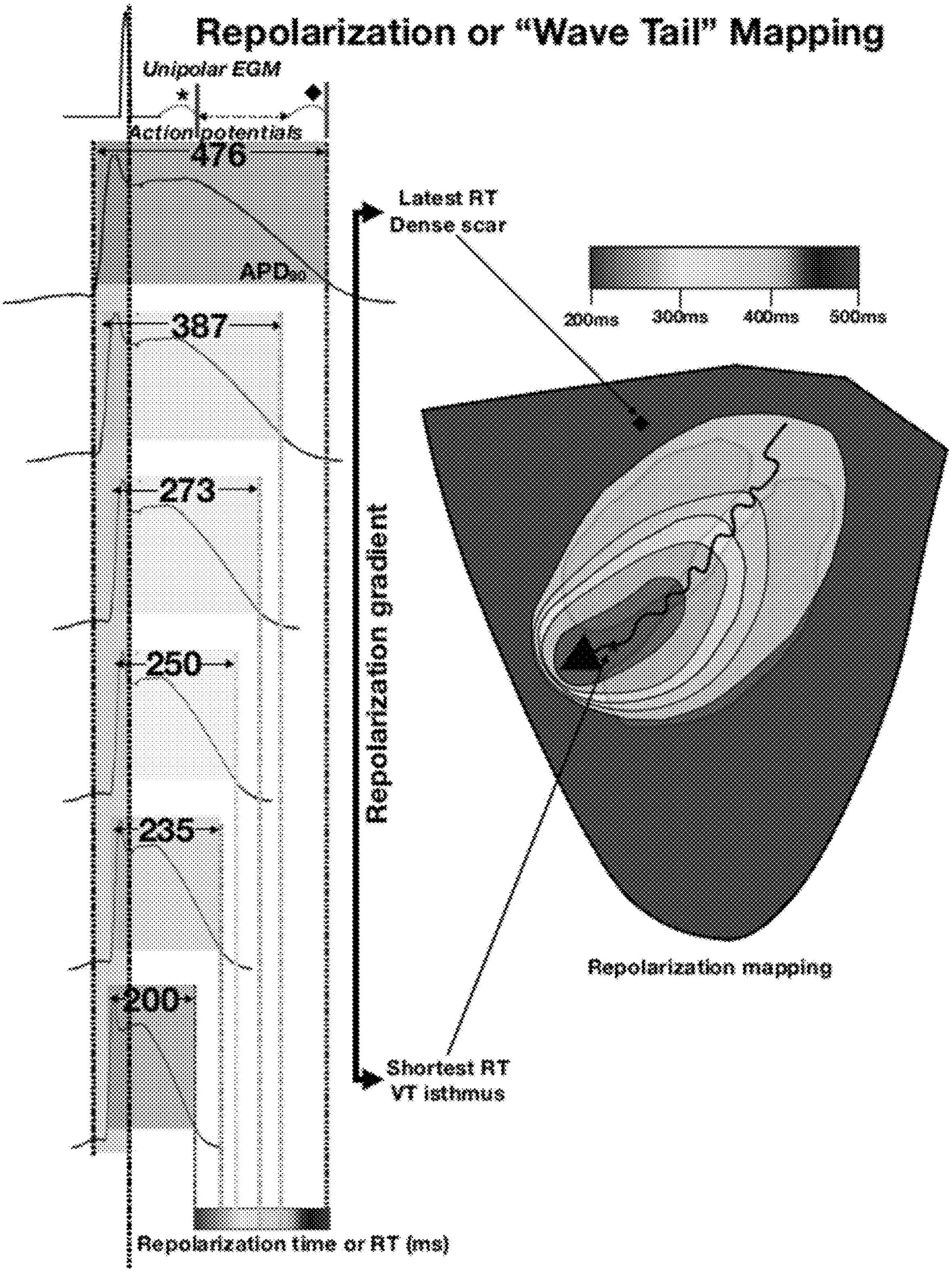
FIG. 1B shows a spatial dispersion of repolarization is shown, where long RTs are seen in dense scar and short RTs and steep repolarization gradient in the critical isthmus.

It should be noted that the mapping efforts detailed in the studies discussed in the background are retrospectively, manually annotated unipolar EGMs, and are not live active mapping schema. Expanding from this preliminary work, the practicality of accurate AT, RT and ARI measurement may need to be considered including optimization of unipolar filtering settings in high-density maps and in different scar types. Developing wave tail mapping and assessing repolarization in a live mapping schema similar to an activation paradigm may aid in the clinical applications of repolarization. For example, an overview of traditional depolarization or "wavefront" mapping techniques including substrate and activation or entrainment mapping (e.g., FIG. 1A). Conceptual representation of repolarization or "wave tail" mapping and annotation of the repolarization time (RT) as a surrogate of action potential duration (APD). A dispersion of repolarization is shown, where long RTs are seen in dense scar and short RTs and steep repolarization gradient in the critical isthmus (e.g., see FIG. 1B).

Although there has been a large body of work demonstrating repolarization heterogeneity in experimental animal studies, more study is needed to corroborate similar findings in human. Furthermore, prospective evaluation of the ability of repolarization mapping techniques to localize critical ventricular substrate, the impact of ablation-based modification on clinical outcomes and direct comparisons to conventional wavefront mapping techniques may be useful for clinical adoption. For example, aside from VT inducibility, a useful additional procedural endpoint may be post ablation remapping to assess physiological modification and homogenization of repolarization within the targeted area.

Figure 2A:
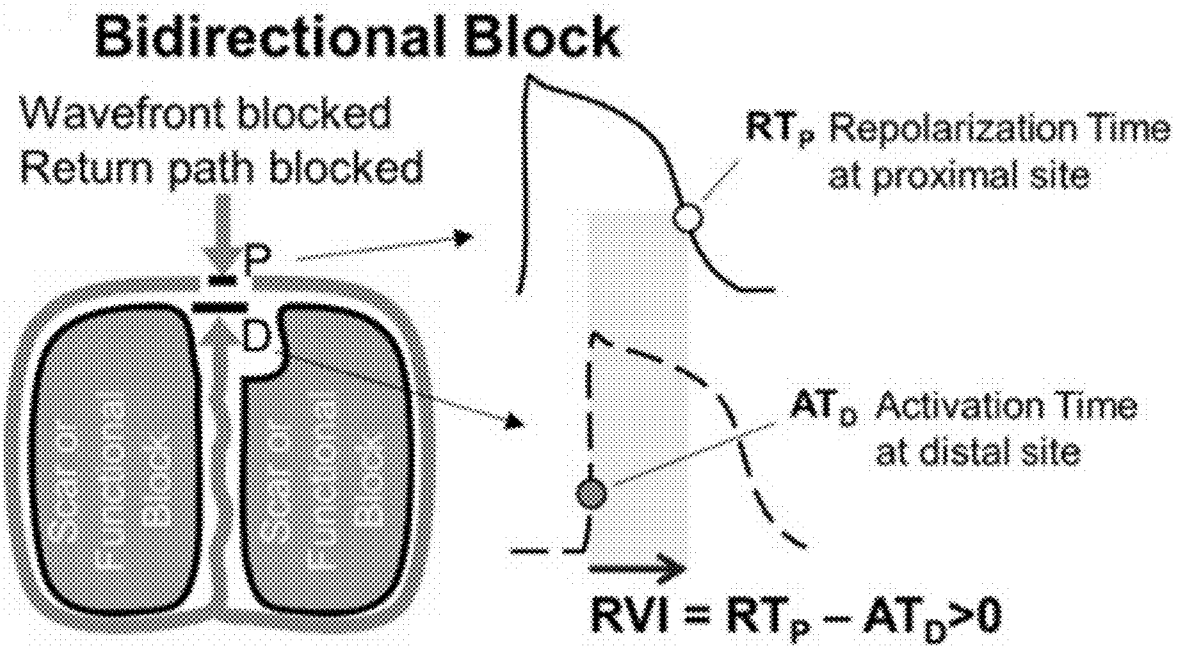
FIG. 2A-2B show a theoretical model underpinning the reentry vulnerability index (RVI) where a re-entrant wavefront that is blocked (RT at point P longer than AT at point D=large RVI) is shown in FIG. 2A, while a re-entrant wavefront that conducts and enables a re-entry (RT at point P shorter than AT at point D=negative RVI) is shown in FIG. 2B (source for FIGS. 2A-2B: Orini M, Graham A J, Srinivasan N T, et al. *Evaluation of the reentry vulnerability index to predict ventricular tachycardia circuits using high-density contact mapping. Heart Rhythm* 2020; 14:576-583.).
Figure 2B:
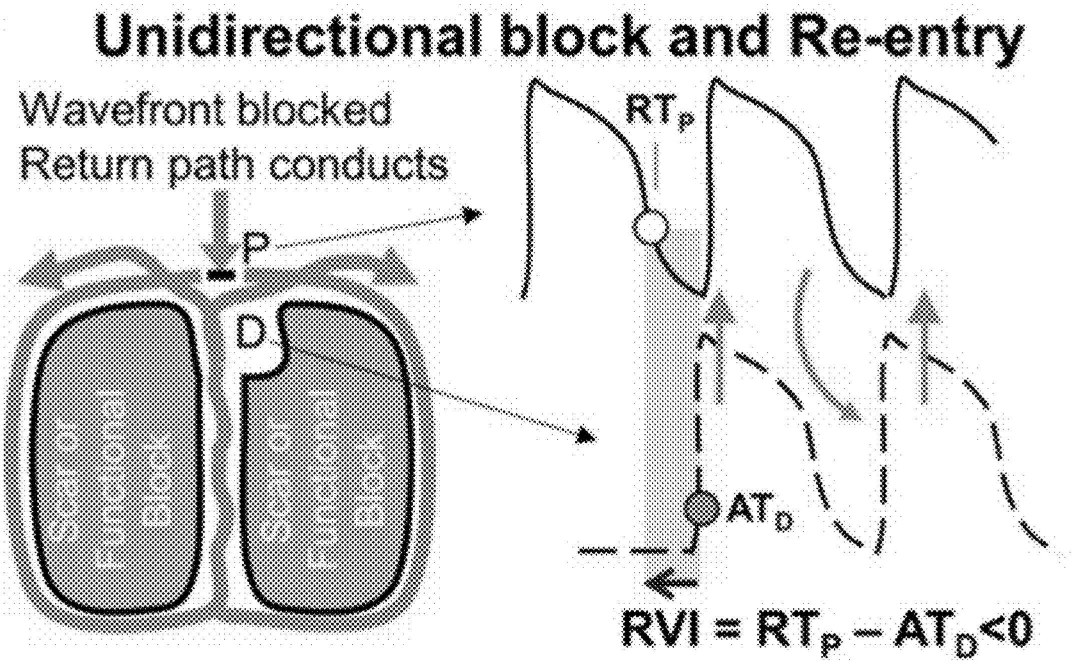

Merging depolarization and repolarization mapping together may provide the most value in assessing cardiac tissue vulnerabilities to abnormal reentrant arrhythmia. For example, regions of depolarization abnormalities also harbor repolarization changes. In fact, reentry vulnerability index (RVI) is a measure where timing of repolarization (APD90) of 'proximal' tissue with S2 is subtracted from the start of S2 depolarization in 'distal' tissue. RVI is a conceptual model integrating both activation and repolarization alterations. For example, FIGS. 2A-2B show a theoretical model underpinning the reentry vulnerability index (RVI). FIG. 2A shows a re-entrant wavefront that is blocked (RT at point P longer than AT at point D=large RVI), while FIG. 2B shows a re-entrant wavefront that conducts and enables a re-entry (RT at point P shorter than AT at point D=negative RVI). FIGS. 2A-2B are reproduced from Orini et al.[32]

Theoretically, for the fundamental prerequisite of unidirectional block to occur and permit re-entry around a fixed or functional block, the repolarization time (RT) of the antidromic wavefront must be shorter than the activation time (AT) of the returning or orthodromic distal wavefront (i.e., RVI=RT−AT<0). If the RT is longer than the AT, then a bi-directional block ensues. Orini and colleagues[32] have outlined a novel use of RVI to identify critical VT sites in 18 patients with ischemic and non-ischemic cardiomyopathy. VT exit sites were determined in the majority of cases with pacemap mapping (67%) and the remainder with activation/entrainment (33%). High-density substrate maps were created using a multipolar catheter during ventricular extra-stimulus mapping (either single or using a drive train) to further expose channels of slow conduction. Retrospective analysis of each point on the map was performed examining the surrounding points within a predefined radius of 8 mm. As the shorter RVI is more likely to allow reentry, the shortest RVI from the surrounding points was annotated and a color-displayed RVI map created.

Figures 3D, 3E:
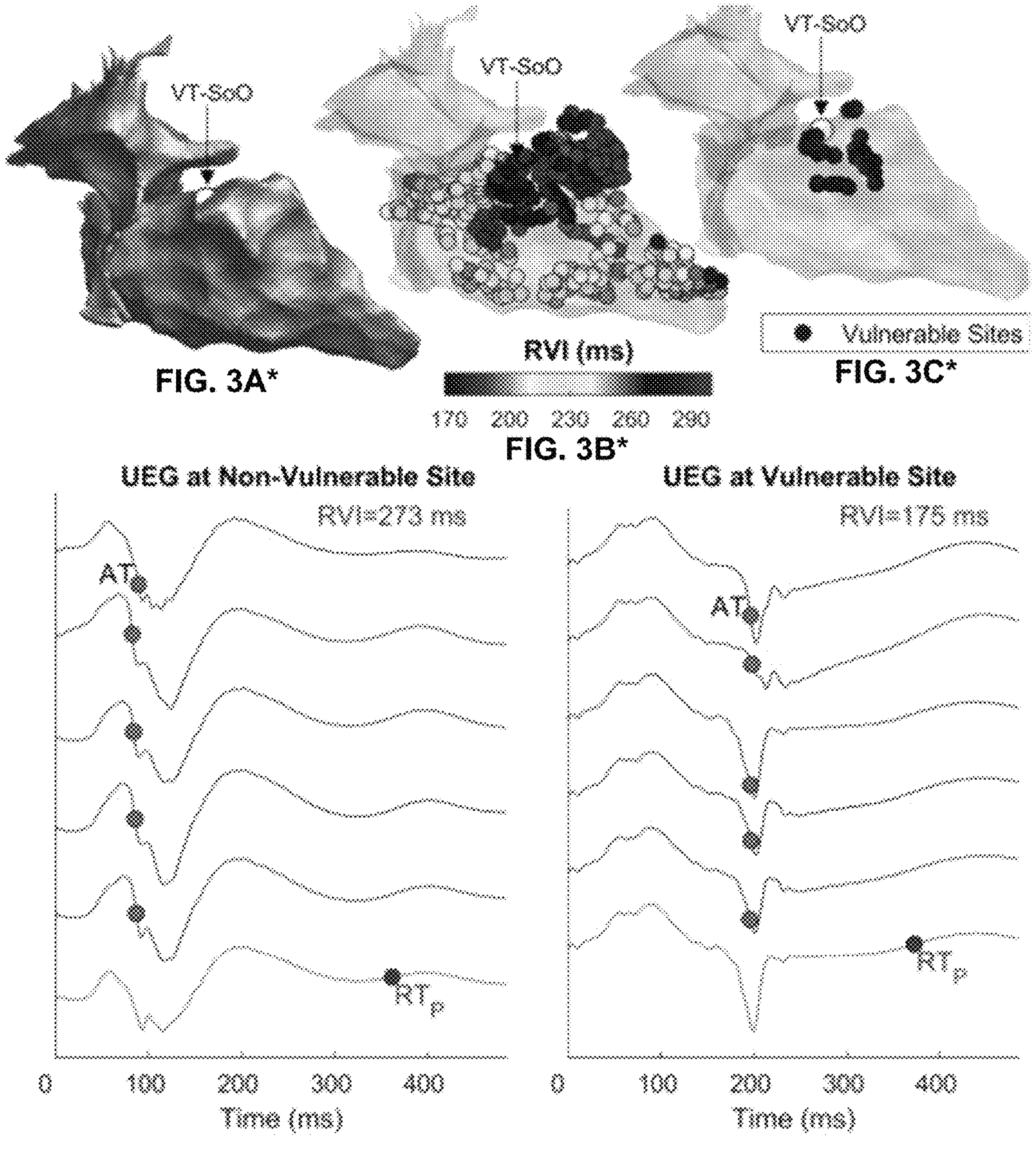

For example, FIGS. 3A-3E show examples of reentry vulnerability index (RVI) identifying vulnerable sites close to an entrained ventricular tachycardia (VT). In particular, FIG. 3A shows an anatomic map showing the VT site of origin (VT-SoO) as a white dot. FIG. 3B shows an RVI map where each dot represents a cardiac, site and RVI is color-coded. FIG. 3C shows a of sites with the lowest 5% of RVI values. FIGS. 3D and 3E show unipolar electrograms (UEGs) from an electrode site showing high (FIG. 3D) and low (FIG. 3E) RVI (the bottommost curves in each graph) and from neighbouring electrode sites (the five upper curves in each graph). The circles represent repolarization time (RT) at the site of RVI measurement ($RT_P$) on the bottom curve of each graph and activation time (AT) at neighbouring sites, respectively, on the upper five curves of each graph. FIGS. 3A-3E are reproduced from Orini et al.[32]

In the example shown in FIGS. 3A-3E, AT, RT and ARI were calculated for each point. As the activation time window of interest ended after QRS duration, EGMs with complex morphologies and late components typically seen within the perimeter of scar may have been automatically excluded. Even within this limitation, VT 'exit sites' which are commonly located just outside the scar regions were localized with reasonable accuracy. Interestingly, RVI was the most accurate index when all other activation-repolarization markers were assessed where AT and ARI were in closest proximity to RVI. The overall accuracy of RVI to localize the critical VT site (within 10 mm) was 72.2%, whereas in 5.6% of cases, the shortest RVI was incorrect and remote. This may be because such patients often have more than one potential VT isthmus. In this study, RVI was the least inaccurate index compared to AT, RT and RVI. Prospective empirical targeting of low RVI sites was not performed in this study due to the lack of ability perform real-time wave tail mapping.

A unique feature is that RVI will not only identify the critical VT site involved in the clinical VT, but all possible sites susceptible to re-entry. Due to selective mapping, studies have not evaluated the possibility of global repolarization mapping strategy in detail. Using non-contact RV mapping, the same group has previously also demonstrated RVI closely co-localizes the endocardial VT exit sites in patients with arrhythmogenic right ventricular cardiomyopathy and Brugada syndrome.[33] Additionally, the role of the RVI being a 'global' indicator (RVIG) of vulnerability to re-entrant arrhythmias was explored and it was found that a lower RVIG was associated with inducible VT and clinical VT events during follow-up. Further support for its mechanistic underpinning relating to detecting susceptible regions of unidirectional conduction block and local re-entry is evidenced by its inaccuracy to detect focal ventricular sources caused by automatic or triggered activity.

Repolarization can be analyzed using a multitude of techniques. Refractory period determination focuses on calculating the re-excitation phase after extra-stimuli delivery but is limited by the onerous need to test at each individual site. Unipolar measurement of potential APD gradients omits the 3-dimensional contribution of repolarization. ARI is a clinically useful method as it correlates to APDs as determined by both refractory period determination and mapping using intracellular electrodes, but potential errors in anisotropic membrane potentials and inconsistent coupling resistances reduce its accuracy. Furthermore, non-specific T wave changes in diseased tissue, for example: biphasic, flat, multicomponent signals make accurate measurement very challenging. Measurement of monophasic APs with contact or intracellular electrodes is limited by the potential damage to the underlying tissue as well as difficulty to use in the beating heart.

Optical mapping has been shown to correlate to intracellular electrode-measured APs.[34] Compared to unipolar and bipolar EGMs, the major advantage of optical mapping is the provisions of uniform high-density signals that have no far-field contamination and is independent of wavefront directionality. The major downside of optimal mapping is the inability to apply it in a clinical setting. However, determination of the voltage-dependent response is well described. Firstly, depolarization is typically defined as the maximum first derivative of the AP upstroke $(dV/dt)_{max}$. Although no clear definition is used for determining repolarization, most use values of the AP downstroke to baseline (either 50%, 75% or 90%). Alternatively, the peak of the second derivative $(d^2F/dt^2)_{max}$ has been shown to be a practical and reliable time point in repolarization. In an optimal mapping animal study supplemented by detailed evaluation of fiber orientation to record activation and repolarization wavefronts from the endocardium and epicardium, Kanai and Salama[35] showed that epicardial repolarization indeed spreads anisotropically and is convincingly determined by epicardial fiber arrangement. Here, repolarization patterns were not influenced by pacing rate, site or engagement of the Purkinje system and was reproducibly initiated from the apex, indicating that apical cells have the shortest APD, independent of the myocardial contractible state. Epicardial repolarization patterns were not a result of a phase wave due to intrinsic repolarization of individual cells, but were spread from cell-to-cell, linked by intracellular electrical coupling, analogous to ventricular activation. Endocardially, the first sites to depolarize were the first sites to repolarize. However, due to heterogeneity in APD, random repolarization patterns were seen.

It is contentious as to whether a wave tail is truly a 'wave', electrically coupled at a cellular level or only appears as a phase wave due to independent repolarization of individual cells. In experimental studies, multiple lines of evidence suggest a wave tail is a true wave. The repolarization anisotropic spread along the direction of myofiber orientation, strongly reproducible beat-to-beat repolarization patterns and slow velocities driven by the AP downstroke, repolarization that is pacing and Purkinje activation site independent as well as alternation of repolarization to random patterns during hypoxia all support the view that repolarization is not a phase wave.[35] In mathematically modelled data, APDs have been shown to be modulated by low resistance cell-to-cell electrical coupling where APD variation equalizes under normal conditions but increases along with resistance in the setting of ischemia and cellular uncoupling.[36,37]

The current state of clinical wave tail mapping is rudimentary, as it has mostly been used in experimental situations since optical mapping is not possible in the clinical setting. Its limited use in human studies requires post hoc analysis. Only monophasic action potential (MAP) mapping provides real-time assessment, but point-by-point ARI is post hoc thus not allowing for true wave tail mapping. Non-invasive epicardial mapping using electrocardiogramaging is currently limited in its accuracy to be reliably used for this purpose. A recent direct comparison of non-contact ECG Imaging (ECGI) to epicardial contact mapping points demonstrated only moderate correlation of unipolar morphology, with AT and RT maps having a displacement error of approximately 13 mm.[38] The largest errors were in the accurate measurement of ARI due to T wave morphology variability and the accurate identification of the dV/dt max in the T wave upstroke. Aside from the challenges in optimizing and simplifying clinical wave tail mapping, there are other obstacles. For instance, as wave tail mapping examines local repolarization that occurs at a lower frequency and over a longer time scale, annotation is prone to errors due to contamination of other low frequency waveforms (for example, far-field activation, respiration, cardiac motion, ambient electrical noise of recording systems). The 'smudging effect' is certainly relevant in a heterogeneous tissue where timing of local repolarization cannot be easily defined and perhaps even harder to determine than time of local depolarization in a multi-component bipolar EGM.

Signature surface 12-lead ECG atrial or ventricular T wave morphologies of different exit sites (relevant for pace-mapping) are also unknown. In fact, patterns of summated repolarization vectors of different exits may not be resolved purely on the body surface using a standard 12-lead ECG bandwidth. Additional tools such as ECGI may be needed. ECGI may also be used to non-invasively determine ARIs, regions with increased repolarization dispersion or abnormalities and guide the response post therapeutic intervention such as antiarrhythmic therapy or catheter ablation.[39]

Based on the above challenges, there is currently controversy in determining the time of local repolarization. Using action potential recordings with potassium-loaded microelectrodes and Laplacian EGM analysis, time of local repolarization on unipolar EGMs has been shown to coincide with the upslope of the local T wave. In addition, biophysical recording variables (electrode size, interelectrode spacing, orientation, far-field contamination) that are known to influence unipolar and bipolar EGM waveforms will be relevant for repolarization mapping. Furthermore, assessment of the effect of bipolar directionality on repolarization markers may be needed, especially given scar anisotropy.[40] However, fixed-grid electrode platforms (the ADVISOR™ HD Grid, Abbott Laboratories and OPTRELL™, Biosense Webster) are a paradigm shift in cardiac mapping permitting direction-aware solutions to reduce the effect of directional dependency on local assessment of activation.

It should also be noted that annotation of Recovery Time (RT) and Activation Time (AT) in an experimental study or computational model under control experimental conditions is a different task compared to accurately and reliably measuring RT and AT from unipolar EGMs in a clinical setting. As such, this concept has not reached meaningful clinical utility yet, and this idea has essentially been an academic concept rather than a therapeutic tool. The errors in annotation also stand as a huge barrier. Inherent to the current conventional paradigm over and above practical accurate annotation due to the averaging of the moment of repolarization using far field unipoles and filtering that essentially argues against the ability of current methods to truly determine local repolarization, while using such tools. There are also instrumentation and signal processing challenges.

Accordingly, in one aspect of the teaching herein, there is provided an innovative approach to map the wave tail and assess truly local repolarization, which can be validated against concurrent optical mapping from the same anatomic location. The electrical repolarization measure determined according to the teachings herein which involves: (a) the acquisition of bipolar EGMs using orthogonal electrodes, or (b) the use of a vectorial approach that may both provide local assessment of repolarization.[41]

Figure 4:
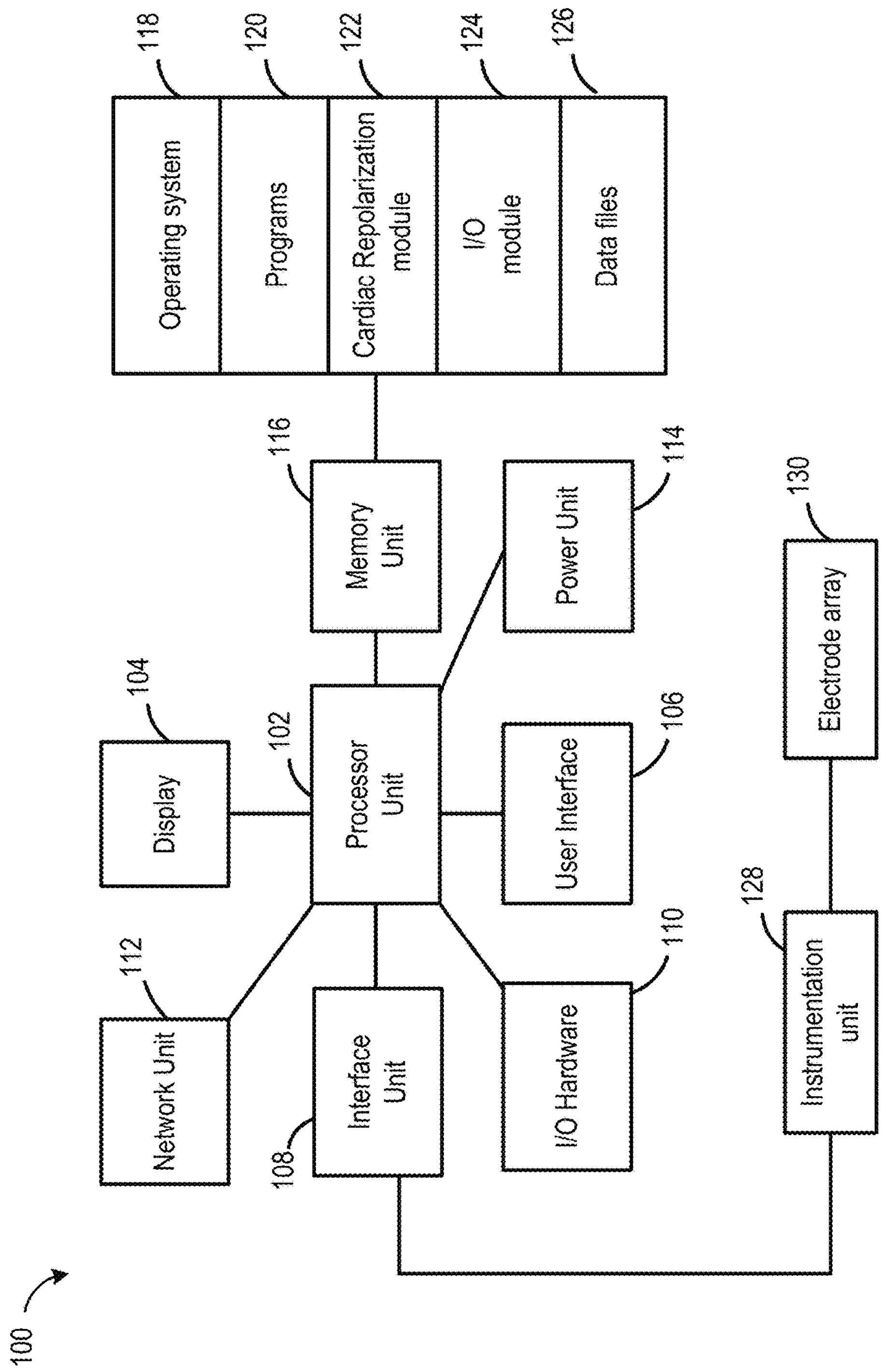
FIG. 4 is a block diagram of an example embodiment of a system for determining cardiac repolarization in accordance with the teachings herein.

Referring now to FIG. 4, shown therein is a block diagram of an example embodiment of a system 100 for use in determining repolarization in accordance with the teachings herein. The system 100 generally includes a processor unit 102, a display 104, a user interface 106, an interface unit 108, input/output (I/O) hardware 110, a network unit 112, a power unit 114, and a memory unit (which may also be referred to as a "data store") 116. The system 100 further an instrumentation unit 128 and an electrode array 130. In other embodiments, the system 100 may include additional components, fewer components or different components as long as the functionality described herein is provided.

In general, a user may interact with the system 100 to perform a variety of functions including, but not limited to, measuring repolarization, performing repolarization mapping and/or electrical stimulation for a patient's heart.

Accordingly, the majority of the components of the system 100 may be an electronic device or computer system that is coupled to the instrumentation unit 128 and the electrode array 130, which may be used by a user, such as a medical practitioner or surgeon, to perform a medical procedure for measurement, diagnosis and/or treatment purposes.

The processor unit 102 controls the operation of the system 100 and can be any suitable processor, controller, or digital signal processor that can provide sufficient processing power depending on the configuration, purposes, and requirements of the system 100. For example, the processor unit 102 may include a standard processor, such as an Intel or AMD processor. Alternatively, there may be a plurality of processors that are used by the processor unit 102, and these processors may function in parallel and perform certain functions. Therefore, the processor unit 102 is considered as having at least one processor.

The user interface 106 may be used to generate a set of windows or graphical user interface (GUI) screens that can be used to display certain information to the user and receive values for input or control parameters from the user. Alternatively, the user interface 106 may include input devices that a user can use to provide data or control inputs to the system 100. These input devices include a keyboard, a mouse, a touchscreen, other suitable input devices or any operable combination thereof. The user interface 106 can also include devices to provide an output to the user, such as the display 104, a printer, a speaker, other suitable output devices or any combination thereof. The display 104 may be, but is not limited to, a computer monitor, an LCD display, or a touchscreen monitor.

The interface unit 108 can be any interface that allows the system 100 to receive data from or send control signals to other devices or hardware such as the instrumentation unit 128. In some cases, the interface unit 108 can include a serial port, a parallel port, a USB port that provides USB connectivity, another suitable communication port for sending and receiving signals or any operable combination thereof.

The network unit 112 may be a standard network adapter such as an Ethernet or 802.11x adapter or another type of adapter. Accordingly, the network unit 112 can also include at least one of an Internet connection, a Local Area Network (LAN) connection, an Ethernet connection, a FireWire connection, a modem connection, or a digital subscriber line connection. Alternatively, or in addition, the network unit 112 include a wireless unit. For example, the network unit 112 can include a radio that communicates utilizing CDMA, GSM, GPRS, or Bluetooth protocol according to standards such as those in the IEEE 802.11 family (e.g., 802.11ac). The network unit 112 can be used by the processor unit 102 to communicate with other devices or computers.

The memory unit 116 may store the program instructions for an operating system 118, programs 120, a cardiac repolarization module 122, an I/O module 124 and data files 126. The programs 120 comprise program code that, when executed, configures the processor unit 102 to operate in a particular manner to implement various functions and tools for the system 100. The cardiac repolarization module 122 comprises program code that may be used to operate the system in a certain mode so that the instrumentation unit 128 and electrode array 130 are used to perform certain functions as is described in more detail with respect to FIGS. 5A to 5C. The I/O module 124 includes programs for receiving input data from the user or any sensor data obtained by the electrode array 130 that are preprocessed by the instrumentation unit 128. The I/O module 124 may also be used to provide output data to the user, which may be done through outputting text and/or graphics to the display 104 and/or user interface 106 or by sending electronic messages and data via the network unit 112. Any sensor data that is obtained by using the electrode array 130 may be stored in the data files 126. Other items such as operating parameters and/or calibration parameters may be stored in the data files 126.

The instrumentation unit 128 may include hardware and firmware for preprocessing sensor data that is obtained using the electrode array 130 from a patient or subject, which may optionally be done in response to certain stimuli that is generated using hardware included in the instrumentation unit 128. Data acquisition parameters including sampling rate and sampling time periods which are periods of time during which the sensor data is obtained by the system 100 may be specified by the user or be predefined. Accordingly, the instrumentation unit 128 comprises hardware circuitry that is used to improve the quality of the data obtained using the electrode array 130 from the patient or subject. For example, the instrumentation unit 128 may contain at least one amplifier, at least one filter, and an Analog Digital Converter (which may have multiple channels) for amplifying, filtering, and digitizing the sensor data (e.g., sensed cardiac signals). Conventional amplification and filtering may be used. The instrumentation unit 128 may include either at least one single-end amplifier for measuring unipolar electrograms or alternatively may include at least one differential amplifier for applying differential amplification when measuring bipolar electrograms. Both of these types of amplifiers may be multi-channel amplifiers.

The instrumentation unit 128 also includes I/O connections for connecting with hardware for generating signals that can be provided as stimuli to the patient. This external hardware may include, but is not limited to, a stimulus signal generator and stimulator devices (both not shown), for example. The instrumentation unit 128 may include circuitry for preprocessing any stimulus signals that are generated according to stimulus instructions received from the processor unit 102. For example, these stimulus signals are generally amplified, filtered and converted from digital to analog before being sent to the electrode array 130. Accordingly, the instrumentation unit 128 may include programmable hardware that is used for preprocessing the stimulus signals before they are sent to the patient, where the hardware may include, but is not limited to, one or more amplifiers, one or more filters and digital to analog convertors (DACs) or a multi-channel DAC. The stimulus instructions may include values for amplitude, pulse duration, number of pulses, repetition frequency and the like, as is known by those skilled in the art. For example, the processor unit 102 may be configured to control the instrumentation unit 128 and the stimulus signal generator to generate and send stimulus signals to the electrode array 130 for applying one or more stimuli to the cardiac tissue. The stimulus signals may be generated and delivered to the heart of a patient or subject prior to obtaining cardiac sensor data from the electrodes. Alternatively, there may be cases where no stimulus data is provided, and cardiac sensor data is obtained spontaneously.

The instrumentation unit 128 may also include isolation circuitry and some form of circuit breaker of cutoff switches to prevent sending stimulus signals that are too powerful due to glitches, voltage spikes or current spikes to the patient/subject which may injure them as well as protecting other circuitry and hardware from such conditions.

The electrode array 130, which may also be referred to as a multi-electrode array or a gridded electrode array, has a plurality of electrodes that are generally arranged having two or more linear arrays of electrodes where each linear electrode array is spaced apart from an adjacent linear array of electrodes to allow for orthogonal bipolar measurements to be made on the surface of the heart or within the heart. Accordingly, the electrode array 130 may be provided by a suitable catheter electrode array which may have at least two linear arrays of electrodes and electrodes in each linear array are evenly spaced out and adjacent electrodes from two adjacent linear arrays are also evenly spaced out. For example, each linear electrode array may be disposed on a spline. Examples of an electrode array that may be used include, but are not limited to, the ADVISOR™ HD grid from Abbott and the OPTRELL™ from Biosense. Another example of a catheter electrode array which may be used is described in U.S. patent application publication no. 2022/0226637 published on Jul. 21, 2022, which is hereby incorporated by reference in its entirety. The electrodes may be used to obtain unipolar EGMs which may then be processed to obtain bipolar EGMs, or the electrodes may be used to obtain bipolar EGMs.

Figure 5C:
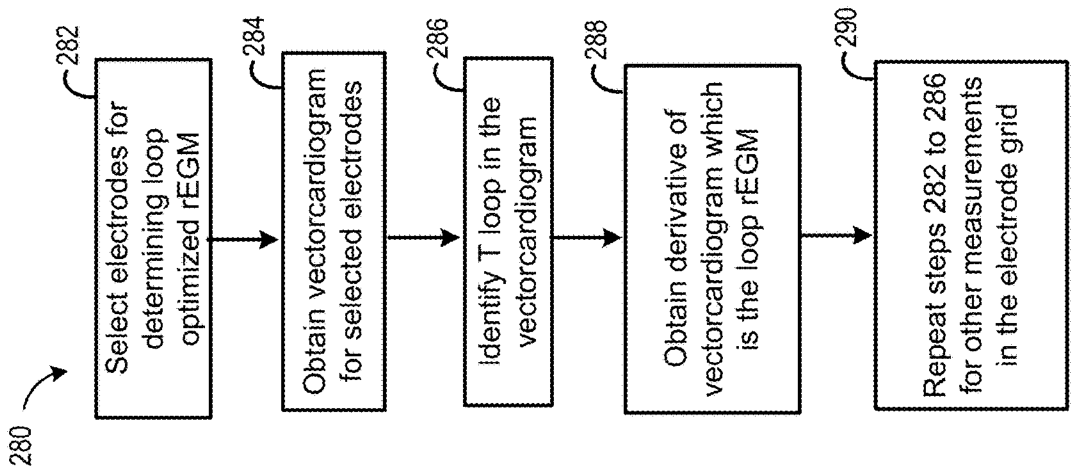
FIG. 5C is a flowchart of an example embodiment of a loop method for determining repolarization enhanced EGMs using an orthogonal bipole loop derived repolarization-optimized EGM (rEGM) method in accordance with the teachings described herein.
Figure 5B:
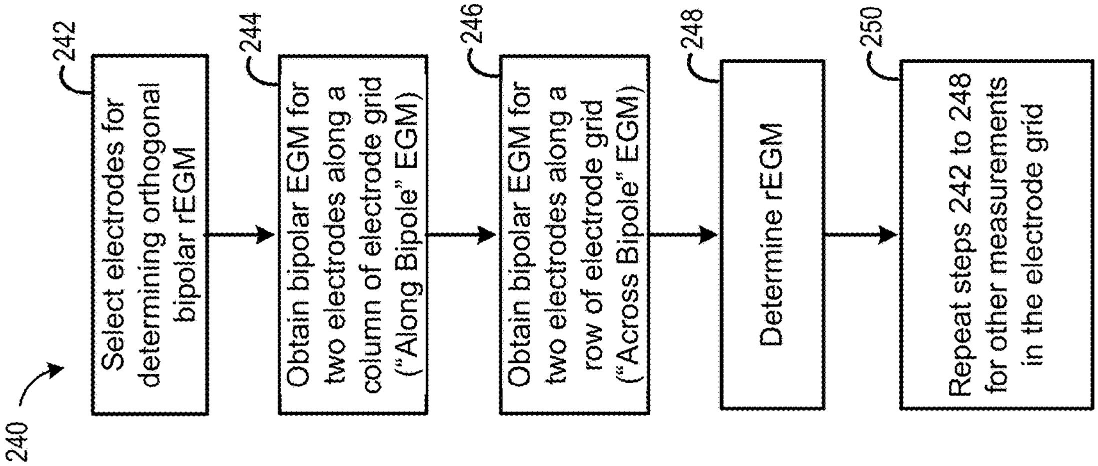
FIG. 5B is a flowchart of an example embodiment of an orthogonal method for determining orthogonal repolarization enhanced EGMs in accordance with the teachings described herein.
Figure 5A:
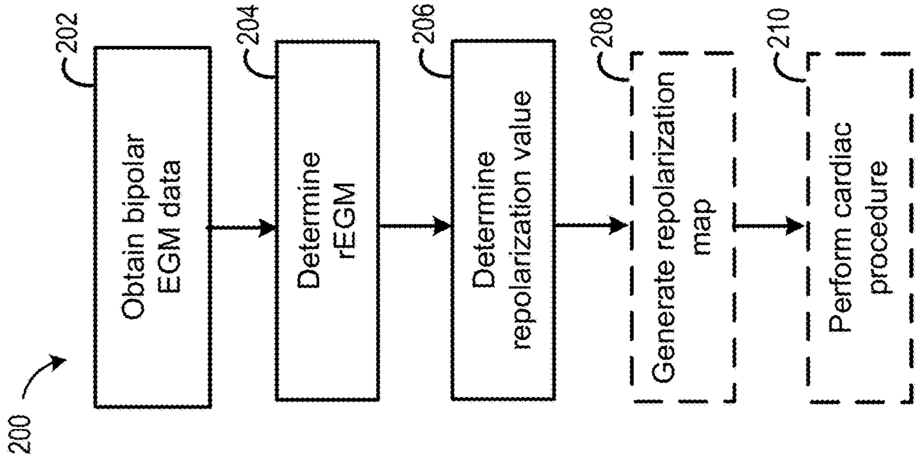
FIG. 5A is a flowchart of an example embodiment of a method for determining cardiac repolarization in accordance with the teachings described herein.

Referring now to FIG. 5A, shown therein is a flowchart of an example embodiment of a method 200 for determining cardiac repolarization in accordance with the teachings described herein. The method 200 uses a novel measurement ($APD^c$-Action Potential Duration) of cardiac repolarization that exploits new features found in gridded catheter electrode arrays.

Figure 6A:
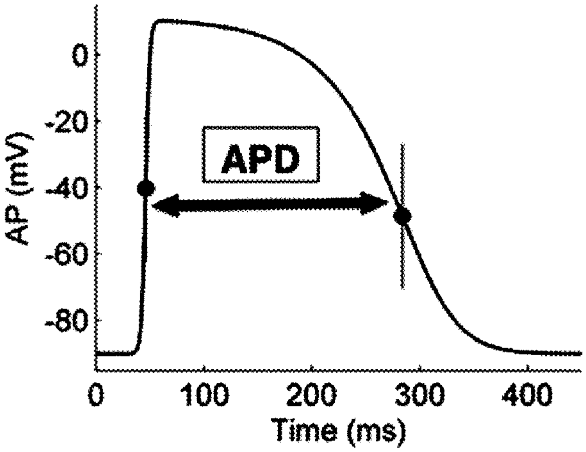
FIG. 6A (Prior Art)
FIG. 6A is plot illustrating Action Potential Duration being measured with a micro-electrode from a single cardiac cell.
Figure 6B:
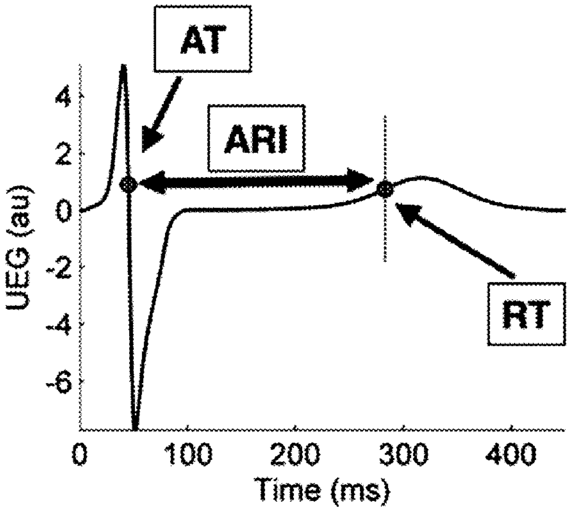
FIG. 6B (Prior Art)
FIG. 6B is a plot illustrating ARI (Activation Recovery Interval) which is a traditional measurement technique for measuring repolarization from a unipolar electrogram.

Traditionally, repolarization time has been measured with a technique known as ARI (Activation Recovery Interval). These are both shown graphically on FIGS. 6A and 6B. In particular, FIG. 6B shows a schematic of the Wyatt method that is used to measure repolarization time (RT) from a unipolar contact electrogram (UEG) from an HD grid of electrodes. The Wyatt method measures ventricular depolarization time as dV/dtmax along the upslope of the unipolar electrogram T wave regardless of polarity (upright or inverted). The RT is measured as the dV/dtmax of the unipolar intracardiac electrogram T wave. The acronym AP represents Action Potential and the acronym AT represents Activation Time (FIG. 6B is from Srinivasan et al. (Heart Rhythm O2 2021; 2:280-289).

However, the conventional ARI method is difficult to use in clinical settings because the UEG suffers a sensitivity to high-frequency noise (60 Hz AC power) and is affected by far field contribution. This latter problem implies that what is being measured might not always be related to local information, but instead include information due to a global effect that is not only not useful but may also mask the important local information.

This problem with UEG is well known and for this reason, bipolar EGMs are the preferred tool for electrophysiologists. The bipolar EGM takes the difference between two adjacent unipolar EGMs. In other words, the bipolar EGM data can be obtained by subtracting EGM data for a first electrode from EGM data for a second electrode where the first and second electrodes are adjacent to one another in the electrode array. However, bipolar EGMs have their own problems, the most important being their sensitivity to wave direction (Josephson & Anter: Substrate Mapping for Ventricular Tachycardia: Assumptions and Misconceptions. JACC: Clinical EP Vol. 1 No. 5 2015 341-52), though some have evaluated their use for repolarization mapping (Orini et al. Theoretical Assessment of a Repolarization Time Marker Based on the Intracardiac Bipolar Electrogram. Computing in Cardiology 2017; Vol 44).

However, with the advent of gridded electrode arrays, it is now possible to resolve the directionality of the wavefront by combining information from orthogonal bipoles. Omnipoles integrate the bipolar information into a voltage field and allows to resolve wave propagation direction and speed (Deno et al. Orientation-Independent Catheter-Based Characterization of Myocardial Activation. IEEE trans. Biomed Eng. Vol 64, No 5, May 2017 1067-77). This method, while elegant, has some shortcomings as it has several prerequisite criteria that must be met and is computationally expensive.

However, the inventors have created a new orthogonal bipolar method that is simple to implement and does not use omnipoles. The new method provides repolarization measurements using bipolar EGMs and has several advantages including but not limited to: (a) using less complicated signal processing, (b) having more accuracy compared to the unipolar ARI method, (c) being robust for practical use and (d) higher repolarization detectability compared to the unipolar ARI method.

Referring back to FIG. 5A, at step 202, bipolar EGM data is obtained. This may be done based on obtaining cardiac sensor data in real time or by retrieving stored bipolar EGM data if it was previously recorded and stored. In the real-time case, the cardiac sensor data is sensed from a surface or the heart of a patient or test subject using the electrode array 130. Alternatively, the cardiac sensor data may be obtained from a data store if it was previously recorded and stored.

Step 202 may involve acquiring unipolar EGMs and then deriving bipolar EGMs from the unipolar EGMs by arithmetically subtracting one EGM from another. Alternatively, step 202 may involve using an electrode array and instrumentation amplifier that allows for the direct acquisition of bipolar EGMs.

In at least one alternative embodiment, the bipole component is a Laplacian electrogram and the bipolar EGM is derived from a Laplacian operation. In each of the embodiments, the resulting bipolar EMG measures the local signal. For example, to produce a Laplacian electrogram at least a group of 9 unipolar GMs may be organized spatially as a 3×3 matrix. If the electrode array is large enough, one can extend the 3×3 matrix to be a 4×4 matrix or higher. The Laplacian operator is a spatial differential operator as given by:

$$L = \frac{\Delta U}{4} = \frac{1}{4}\left(\frac{\partial^2 U}{\partial x^2} + \frac{\partial^2 U}{\partial y^2}\right).$$

Since the Laplacian is a second-order derivative function, one needs at least 3 points in each dimension for calculation (e.g., at least a 3×3 grid of electrodes). The output of the Laplacian operator is a signal (a Laplacian-derived EGM) that represents the Laplacian of the area defined by the electrodes used in the matrix. Accordingly, the Laplacian EGM is assigned spatially to the location that corresponds with the center of the matrix.

In at least one alternative embodiment, the bipolar EGMs may be determined from a principal component referenced unipole (as opposed to a far field referenced unipole). A similar approach applies to the principal component method. For example, a 3×3 matrix of electrodes may be used to obtain principal components from 9 unipole, but this may also be done for larger size matrices, similar to the Laplacian technique. Accordingly, the principal components are obtained from a group of EGMs. The principal components are then averaged to produce the principal component reference unipole. The unipolar in the center of the group can then be referenced to (e.g., subtracted from) the Principal component average to obtain a bipolar EGM using the principal component technique.

In any of these cases for determining bipolar EGMs, there is some preprocessing which may be done in step 202 to improve signal quality and aid in accuracy for determining at least one repolarization value. Alternatively, for stored EGM data, the preprocessing may have already been done. It should be understood that while the use of the subtraction technique for determining bipolar EGMs is described below, any of the aforementioned techniques for EGM bipolar determination may be used.

One challenge with determining repolarization values accurately is frequency content. Unlike the QRS portion of the EGM, the repolarization portion of the EGM is a slowly changing phenomena. This is a challenge as one source of noise in an EGM recording system is baseline wander due to electrode contact, respiration, and the like as is known by those skilled in the art. Traditionally, this noise is removed with the use of a high-pass filter, which is implemented using an electronic circuit design in the instrumentation unit 128 to remove these low frequencies. However, the inventors have found that high-pass filters that are typically used when obtaining EGM data for conventional purposes should not be used when obtaining EGM data for repolarization mapping. On the contrary, it may be preferable for there to be as little high-pass filtering as possible when obtaining EGM data for determining at least one repolarization value. For example, a high pass filter with a cutoff frequency of about 0.02 Hz or about 0.05 Hz might be low enough to allow for the repolarization portion of the sensed cardiac signals to then be amplified (after filtering) so that the repolarization value may be determined with sufficiently high fidelity. This high pass filtering is also helpful to avoid amplifier saturation and/or A/D converter saturation, which may occur when using A/D converters with low dynamic range. However, in at least one embodiment, when higher resolution A/D converters are used that may have up to 24 bits of resolution, such as Analog Device model AD7768, and a sampling rate that is adequate for performing EGM recordings, this allows for smaller amplification after A/D conversion which may eliminate the need for this electronic circuit for high-pass filtering while retaining the EGM information in the signals.

For even better signal fidelity, the amplification circuitry used in the instrumentation unit 128 may include a pair of high-quality instrumentation amplifiers to determine ortho bipoles which may be used when performing method 250 for determining the orthogonal rEGM and repolarization values. These instrumentation amplifiers may have low gain and wide dynamic range to allow for excursion of the sensed EGMs without amplifier saturation. When the high-quality instrumentation amplifiers are differential amplifiers, one of the amplifiers may be connected to two electrodes locate along linear electrode array or the spline thereby providing the Along Bipolar EGM at its output, while the other amplifier may be connected to two adjacent electrodes across the splines thereby providing the Across Bipolar EGM as its output, where one electrode is common to both amplifiers to provide the same input to both amplifiers.

Figure 7A:
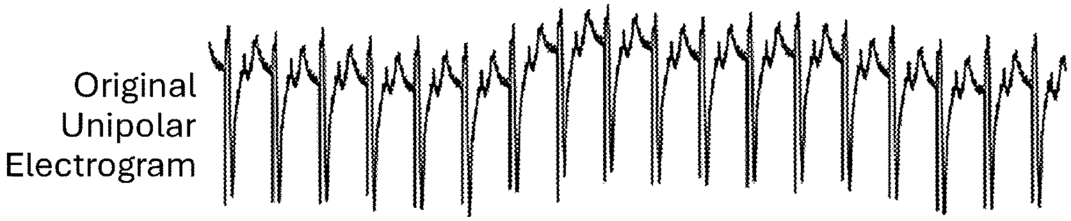
FIGS. 7A-7C graphically show the results from performing baseline correction according to an example embodiment.
Figure 7B:
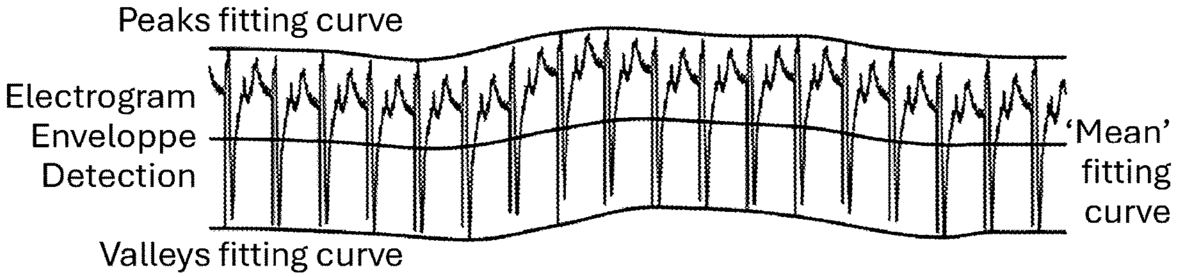
Figure 7C:
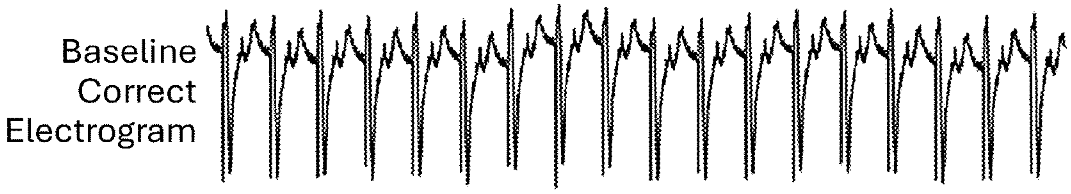

The preprocessing will include performing baseline correction the results of which are shown graphically in FIGS. 7A-7C when performed according to the example embodiment that is now described with unipolar electrograms but also applies to bipolar electrograms directly obtained from instrumentation amplifiers. In the case of unipolar EGMs, this baseline correction may be performed before generating the bipolar EGM from subtracting one unipolar EGM from the other. In the case of bipolar EGMs obtained through hardware, the baseline correction may be used to deal with low-frequency noise that is not sufficiently rejected by an instrumentation amplifier.

Performing baseline correction will remove baseline wandering. FIG. 7A shows a typical, unfiltered unipolar EGM with a roving baseline going down, then rapidly up and then declining towards the end. The EGM also has 60 Hz noise riding over the cardiac cycles. FIG. 7B shows two curves including uppermost and lowermost curves that are a peaks fitting curve and a valleys fitting curve, respectively, and are determined for delimiting peaks and valleys of the unipolar EGM signal that is shown. These peaks and valleys correspond to the maximum and minimum extent of the QRS portions of the recorded signal and the lines are obtained by fitted all of the peak values with a first line and all of the valley values with a second line. These first and second lines corresponding to the upper and lower lines may be referred to as the peaks and valleys curves, respectively. The peaks and valleys curves may be determined using piecewise functions such as, but not limited to, a piecewise hermit function, for example, to connect all of the peaks together and to connect all of the valleys together, respectively. Other functions may also be used in other embodiments including, but not limited to, a cubic spline function or a Bezier line fitting function. A third line may be then computed as the mean fitting curve (i.e., average) of the peaks and valleys curves where this mean line is shown between the peaks fitting curve and the valleys fitting curve in FIG. 7B. The mean line is then removed from the raw unipolar EGM data to provide a baseline-corrected electrogram as seen in FIG. 7C. While this technique may appear similar to standard high-pass filtering, it is actually superior as it does not affect the repolarization component of the unipolar EGM data while compensating for any large baseline drifts.

The peak and valleys may be determined as follows: the electrogram is analyzed with a sliding window, first positioned at the beginning of the electrogram. One peak and one valley are determined from a maximum value and a minimum value, respectively, that are found in the EGM. The window is then moved by its width to a next position that is later in time and another set of peak and valley are detected. The process is repeated until the end of the EGM is reached. The width of the sliding window may be adjusted to adapt the responsiveness of the algorithm to these baseline drifts.

Figure 8A:
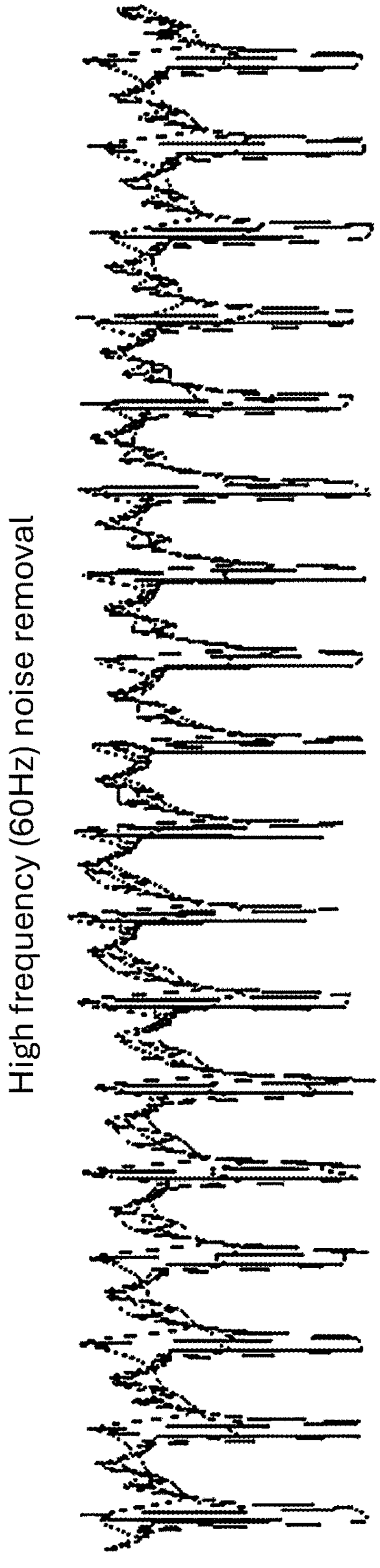
FIGS. 8A-8C graphically show an example of the results of another preprocessing step for eliminating high-frequency noise that is optional and may be performed after performing baseline correction.
Figure 8C:
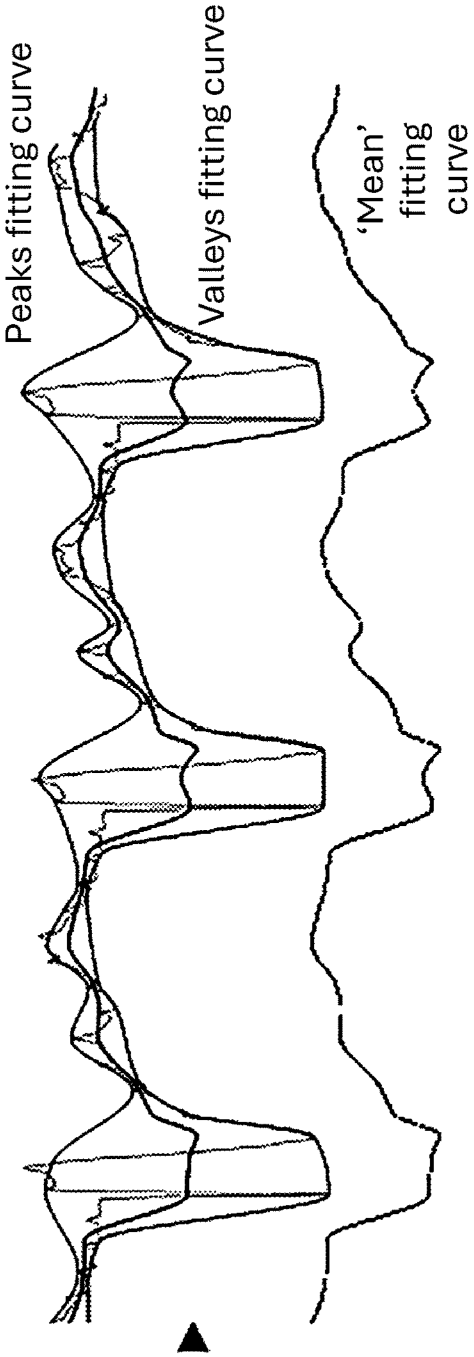
Figure 8B:
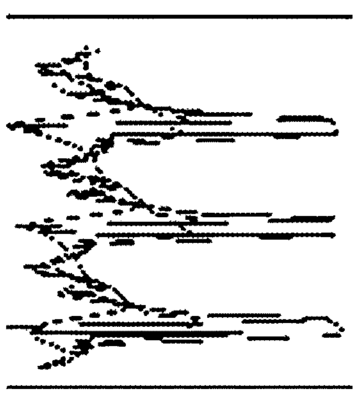

Another preprocessing step, the results of which are graphically shown in FIGS. 8A-8C for an example, that may be performed after the baseline correction step is another noise reduction step, which may be optional in some cases. This noise reduction step is similar to the baseline correction step that was just discussed, except that the mean line is retained for analysis. For example, the EGM may be processed using a sliding window such that local peaks and valleys are identified in the sliding window. The peaks are joined together to form a peak curve and the process is applied to the valleys to form a valley curve, thereby giving two curves roughly delimiting the EGM envelope. A mean value curve is then derived from the mean of the peak and valley curves, providing a new signal call a mean signal that is devoid of high-frequency noise while providing a good approximation of the repolarization segment, as shown in FIG. 8C, which may be processed for $APD^c$ calculation. Alternatively, the reduction/attenuation of the 60 Hz noise may be done using a notch filter as is known by those skilled in the art; however, a notch filter will not eliminate harmonics or other EMI frequencies, such as fluorescent lights, RF generators, heaters and motors.

Referring back to FIG. 5A, the method 200 now proceeds to step 204 where the rEGM is determined, which may be done using one of two methods where each of these methods have been determined in accordance with the teachings herein. The output of step 204 can be one or more compound EGMs (rEGM). For the orthogonal method 240, shown in FIG. 5B, orthogonal bipolar EGMs are obtained and further processed. For example, if three unipolar EGMs are obtained (e.g., recorded) from a set of electrodes that are in positions relative to one another to form a right angle triangle, then a set of orthogonal bipolar EGMs can be derived. For the loop method 280, shown in FIG. 5C, normal EGMs that are not orthogonal may be used.

For example, referring now to FIG. 5B, shown therein is a flowchart of an example embodiment of an orthogonal method 240 for determining a compound orthogonal repolarization enhanced EGMs (also referred to as a compound orthogonal rEGM) in accordance with the teachings described herein.

At step 242, when unipolar EGMs have been obtained and preprocessed as explained previously (e.g., to remove baseline wandering and to remove noise) for step 202, the next step is to select the electrodes where the EGMs obtained by those electrodes will be combined to form orthogonal EGMs including an "Along EGM" and an "Across EGM" which will then be combined to determine the compound EGM for a measurement point in the electrode grid which is formed by the two dimensional arrangement of the electrodes along rows and columns of the electrode array 130.

Figure 9A:
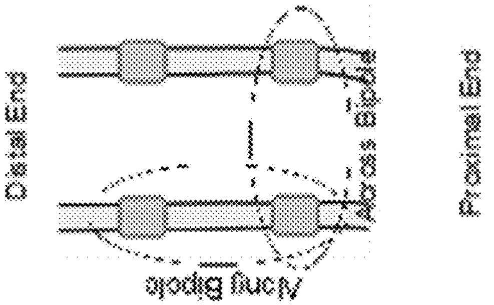
FIG. 9A is a diagram illustrating the electrodes from a multielectrode array that are used to determine Along Bipolar EGMs and Across Bipolar EGMs.
Figure 9B:
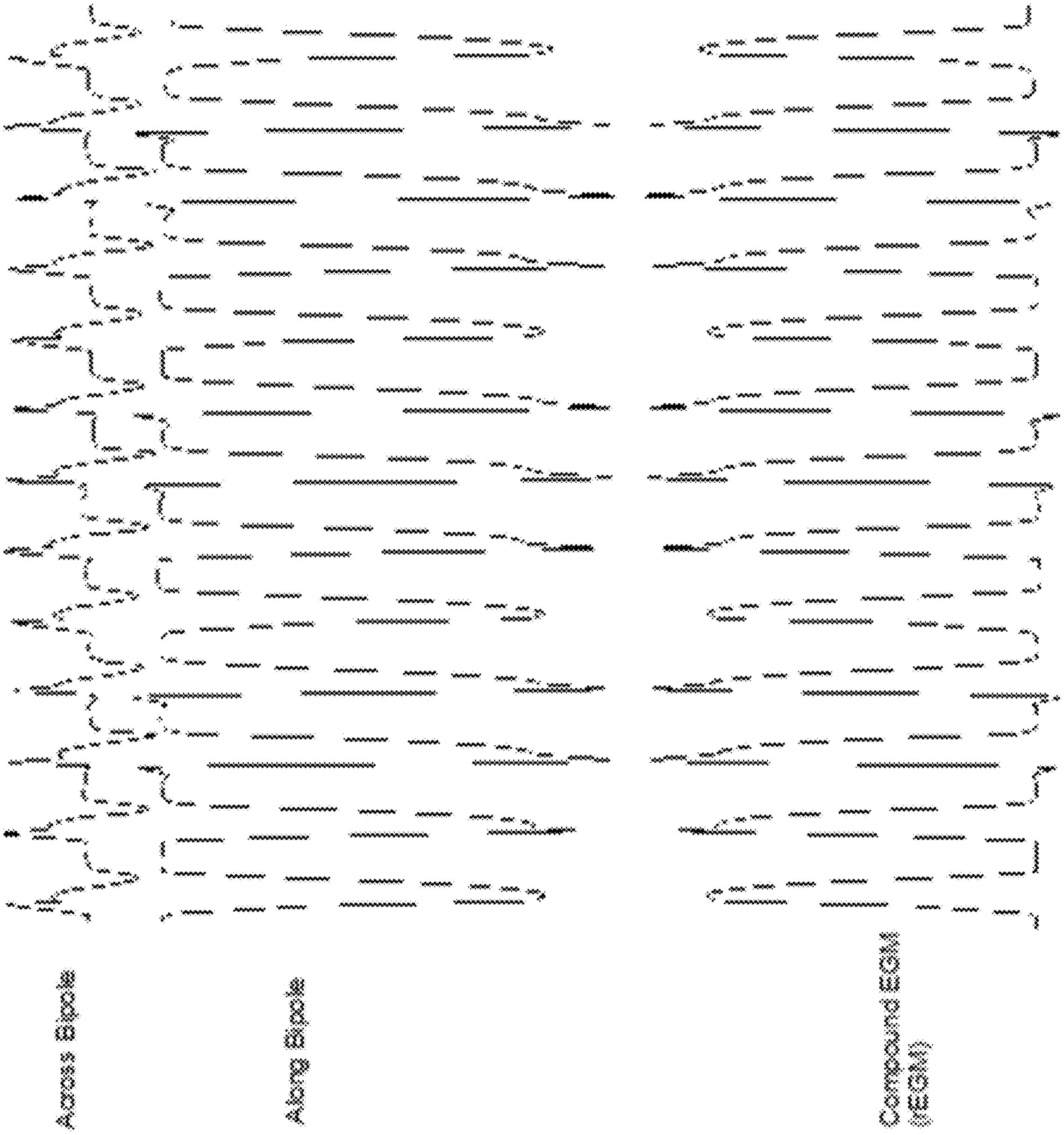
FIG. 9B shows an example of an Across Bipolar EGM in the top graph, an example of an Along Bipolar EGM in the middle graph, and an example of an orthogonal rEGM formed from the Across and Along Bipolar EGMs in accordance with teachings herein.

Accordingly, at step 244 EGM data is obtained from a first pair of electrodes having two electrodes in the same linear electrode array (i.e., along a column of the two dimensional electrode grid). An example of this is shown in FIG. 9A where the first pair of electrodes are used to determine an "Along Bipole" EGM by subtracting the unipole EGM for one electrode in the first pair of electrodes from the unipole EGM for a second electrode in the first pair of electrodes. An example of an EGM determined for an Along Bipolar EGM is shown in the middle panel of FIG. 9B.

At step 246, EGM data is obtained from a second pair of electrodes having horizontally adjacent electrodes from two separate adjacent linear electrode arrays (i.e., along a row of the two dimensional electrode grid). For example, a third electrode from an adjacent linear electrode array where the third electrode is horizontally adjacent to one of the two electrodes from the first pair of electrodes is used to form a second pair of electrodes to determine an "Across Bipole" EGM. An example of this is shown in FIG. 9A where the second pair of electrodes is used to determine the Across Bipolar EGM by subtracting the unipole EGM for one electrode in the first pair of electrodes from the unipole EGM for the third electrode. An example of an EGM determined for an Across Bipolar EGM is shown in the top panel of FIG. 9B.

It is noted that the first and second pairs of electrodes are situated in an orthogonal manner to one another. In addition, the spacing between each pair of electrodes that is used to determine the Along Bipolar EGM is about the same as the spacing between the electrodes that is used to determine the Across Bipolar EGM. This then allows the Along Bipolar EGM and the Across Bipolar EGM to be combined in a mathematically orthogonal manner.

At step 248, the computation of an orthogonal rEGM is performed using the Along Bipolar EGM and the Across Bipolar EGM. This signal may be produced by summing the squares of the Along Bipolar EGM and the Across Bipolar EGM as shown in equation 1.

$$rEGM = \text{Along } EGM^2 + \text{Across } EGM^2 \tag{1}$$

Accordingly, the orthogonal rEGM is a compound EGM that is formed using the bipolar EGMs obtained from orthogonal pairs of electrodes that span a row and column that intersect at the common electrode which is the electrode that is in both the first and second pairs of electrodes mentioned earlier. The compound rEGM may be considered as representing an EGM that is obtained at a midpoint between all three electrodes that area diagonally position with respect to one another. In other embodiments, other equations may be used for generating the compound EGM where the Along Bipolar EGM and Across Bipolar EGM are combined in an orthogonal manner. For example, equation 1 may be modified by taking the square root of the sum of the squares of the Along and Across EGMs.

The method 240 then moves to step 250 where the above-noted process for steps 244 to 248 is repeated many times by moving linearly along the pair of linear electrode arrays to obtain rEGM values for a plurality of locations that are covered by the grid electrode array. This may be considered as moving along one column of the grid array row by row and once the two linear arrays have been traversed in this matter, the measurements are done for a plurality of points using one of the linear electrode arrays that was just used and another linear electrode array which is adjacent to it and hasn't been used for performing these calculations yet.

In the case where bipolar circuitry is used in the instrumentation unit 128 that allows for direct measurement of bipolar EGMs, the aforementioned steps can be somewhat simplified. In this case, the EGMs may be referred to as hardware generated bipolar EGMs. In this case, the same preprocessing step for performing baseline correction may be performed. However, since the instrumentation unit 128 includes differential amplifiers with common mode rejection, in this case, sensor data from two adjacent electrodes in the electrode array 130 can be provided to the differential amplifier which then outputs the bipolar EGM for the two adjacent electrodes. The common mode rejection will remove the 60 Hz noise that is present in the sensor data for both of these adjacent electrodes.

Accordingly, with step 242 electrodes are selected in a similar manner as described previously but in step 244 the EGMs from the electrodes in the same column of the electrode grid are provided to the differential amplifier to obtain the Along Bipolar EGM. Likewise in step 246 the EGMs from the adjacent electrodes in the same row of the electrode grid are provided to the differential amplifier to obtain the Across Bipolar EGM. At this point steps 248 and 250 are performed as previously described.

It should be noted that bipoles obtained in current clinical mapping systems are usually derived from unipolar EGMs, using unipolar amplifiers, that do not offer the same common-mode noise rejection with high pass filters settings produce signal quality for the compound EGM that is used to determine repolarization that may be inferior to hardwire-obtained Bipolar EGMs obtained using instrumentation amplifiers with common mode noise rejection. Future innovations in amplifier hardware, filter design (e.g., such as ringing in the low frequency regions at high pass cut off settings) and wide dynamic-range A/D converters may allow for improved accuracy in repolarization mapping.

Alternatively, another method may be used for determining at least one compound electrogram (EGM). Referring now to FIG. 5C, shown therein is a flowchart of an example embodiment of a loop method 280 for determining repolarization enhanced EGMs using an orthogonal bipole loop derived repolarization-optimized EGM method in accordance with the teachings described herein. This method uses Vectorcardiogram-like loops that are derived from orthogonal sets of bipoles vector loops. The compound EGM that is determined using this technique may be referred to as a loop optimized rEGM.

At step 282, an orthogonal set of electrodes from the electrode array 130. For example, four electrodes may be selected where a first pair of electrodes is in a first linear array and a second pair of electrodes is in a second linear array such that each pair of electrodes are adjacent to one another forming a square. Alternatively, in another embodiment, another arrangement for the electrodes is a triangle similar to what was described in method 240.

At step 284, a vectorcardiogram-like loop is derived from the orthogonal set of bipoles. The vectorcardiogram-like loop is obtained by plotting the Along Bipolar EGM versus the Across Bipolar EGM. Thus, a loop is obtained by plotting one signal versus another signal (i.e., plotting the signal amplitudes that occur at the same time and doing this for all time points). If there is no wave propagating (i.e., a flatline) then the loop plot is a single point. However, typically as the amplitudes change differently in the Along Bipolar EGM versus the Across Bipolar EGM, a loop is produced. Ideally, the beginning and end of the loop are the same point if there is no variation in the baseline for the Along and Across Bipolar EGMs. The largest loop is the QRS while the smaller loop is the T-wave. An example of a vectorcardiogram-like loop (or vector loop for short) is shown in panel E of FIG. 11B. The T loop may be seen as part of the vector loop. In this example, the T loop is a colored loop that is shown and labeled in FIG. 11B.

At step 286, the T loop (i.e., repolarization loop) is identified from the loop diagram so that it is distinct from the QRS loop. This may be done several ways including visually or mathematically.

At step 288, a derivative of the vectorcardiogram is obtained by obtaining the time projection of the repolarization loop along the long axis of the T loop (i.e., the axis where the maximum peak of the T loop resides) where the projection may be called a loop optimized rEGM.

At step 290, if it is desired to obtain a plurality of rEGMs for different sets of electrodes then steps 282 to 286 can be repeated for unique sets of 4 electrodes that form a box shape as described. In addition to, or alternative to, using a planar box shape for the selected electrodes, the selected electrodes may be chosen to form a tetrahedron in 3D space.

When method 240 or 280 is completed, depending on which technique was used to determined rEGM, step 206 is performed where the repolarization value may be determined for one or more of the rEGMs that were obtained. In the case where loop optimized rEGMs were obtained a measurement of repolarization duration, called $APD^v$, may be obtained for one of more of the loop optimized rEGMs. The $APD_v$ is measured from the onset of a QRS complex to baseline return of the loop rEGM. It was thus hypothesized that rEGM provide vector-derived integrated action potential duration ($APD^v$) that correlates with local repolarization assessed by optical mapping. The output of step 206 in this case is one of more $APD^v$ values.

Figure 10:
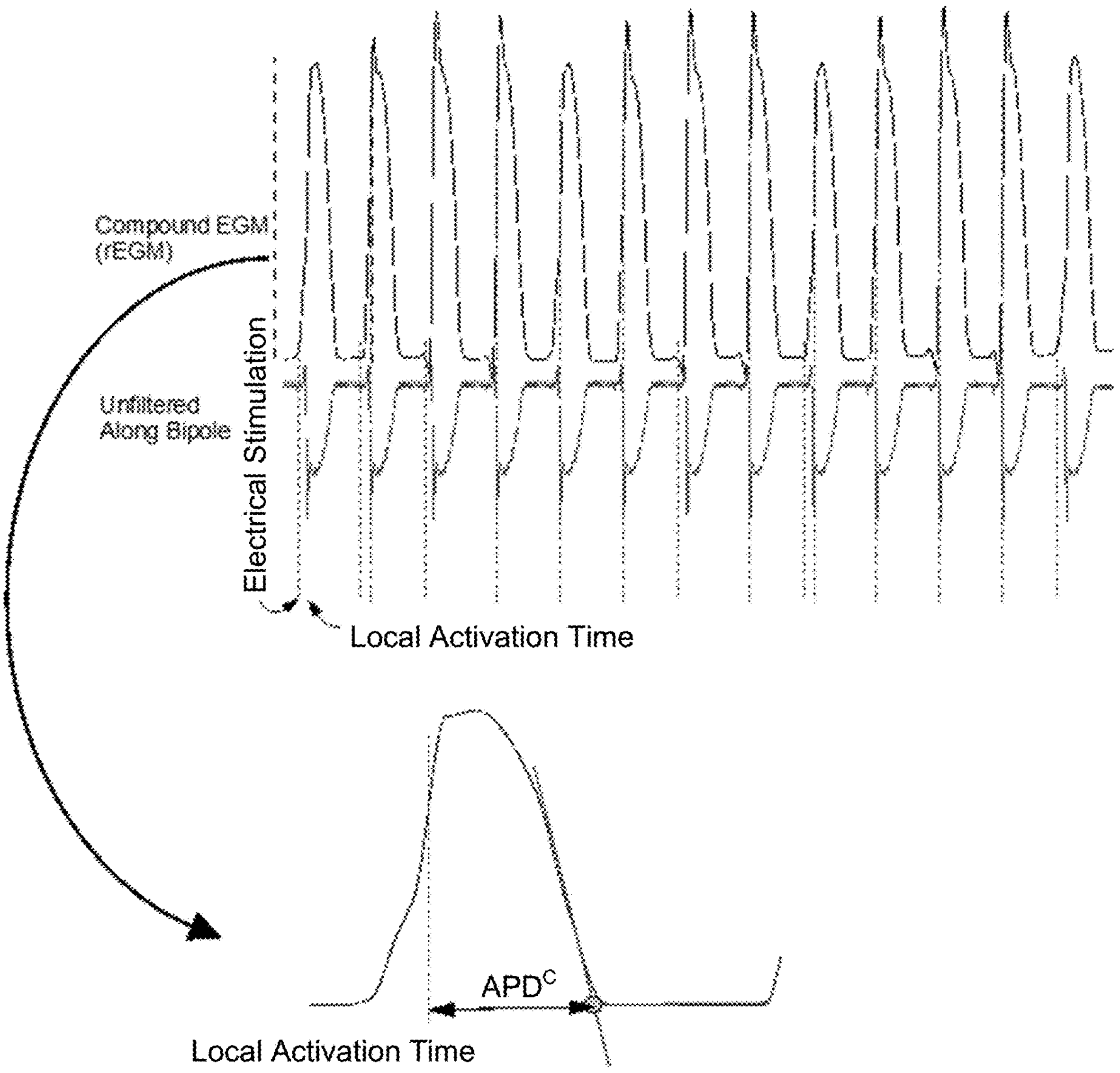
FIG. 10 graphically shows an example embodiment for the determination of $APD^c$.

In the case where orthogonal bipole rEGMs are determined, which may be done using method 240, step 206 involves determination of $APD^c$ as the repolarization value where $APD^c$ represents a measure from the onset of QRS to the baseline return of rEGM. The determination of $APD^c$ is shown graphically in FIG. 10. First, a local activation time is found on a unipolar EGM that has been digitized but not further processed (e.g., the middle curve labelled "Unfiltered Analog Bipole") as is known by those skilled in the art. This may also be done using a bipolar EGM. The local activation time will act as a reference time for $APD^c$. The $APD^c$ is a duration measurement that is the time period between the reference time and the time associated with a fiducial point at the end of the repolarization period. The fiducial point may be determined based on the intersection of two lines including a first line that is in line (i.e., aligned or co-linear) with the diastolic baseline (shown by the horizontal line to the right if the fiducial point in the magnified image at the bottom of FIG. 10) while the second line is aligned with the most negative slope of the portion of the orthogonal bipolar rEGM. The output of step 206 in this case is one of more $APD^c$ values.

Figure 12A:
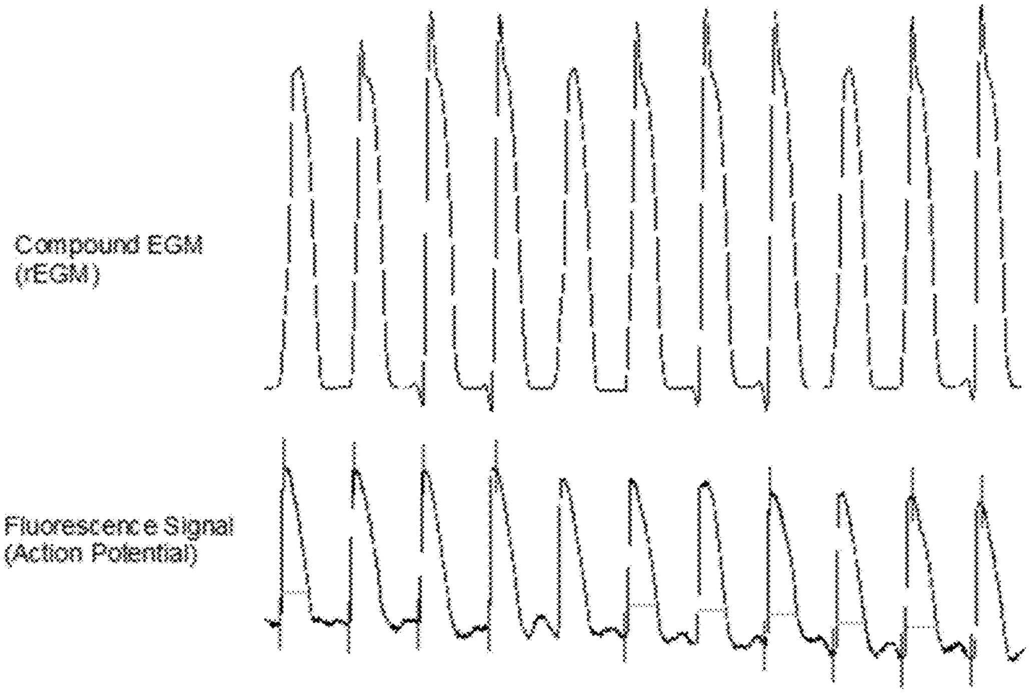
FIG. 12A shows an example of a compound EGM signal obtained using the orthogonal bipolar technique described with respect to FIG. 5B in the top graph and an example of a Fluorescence signal obtained for the same location using the current gold standard.

This method of determining $APD^c$ was validated against a gold standard which was a fluorescence signal obtained from a Langendorff model of a rabbit heart perfused with a potentiometric dye. The fluorescence signal is a good approximation of an action potential and is often used as a gold standard. FIG. 12A below shows an example of an orthogonal bipolar rEGM to be evaluated in the top graph and a fluorescence signal with markers indicating $APD_{80}$ measurements in the bottom graph. This fluorescence signal was obtained during the same experiment, in the middle of the group of 3 electrodes, where the heart was exposed. Further details are provided in the description of the study described with respect to FIGS. 12B and 12C which is a Bland-Altman plot of these two methods and the regression curves of both $APD^c$ and traditional ARI versus $APD_{80}$, respectively, for data points obtained in a series of experiments and under various pacing conditions and medication to create a range of $APD_{80}$ values for comparison.

At 208, the method 200 comprises generating a repolarization map based on all of the repolarization values (e.g., repolarization times) that were determined at step 206. Each repolarization value was determined from a compound EGM (e.g., orthogonal or loop optimized) that was obtained for a given location on the electrode grid. Accordingly, the repolarization values may be plotted for the locations from which the corresponding EGMs were determined. The repolarization map may be displayed on a monitor of a desktop or a display of a laptop or table computer. In addition, or alternatively thereto, the repolarization map be stored in a data store and/or transmitted to another computing device. Step 208 may be optional in some cases.

At 210, the method 200 comprises using the repolarization map or a group of repolarization values for performing a cardiac procedure. For example, tissue ablation and/or tissue debulking may be performed. Tissue ablation may be guided by using the repolarization map. For example, a possible ablation target might be an area where large repolarization gradients are located. Another possible cardiac procedure involving repolarization mapping may be a variant of DeEP mapping (generally described in U.S. Pat. No. 9,662,178) where instead of looking at decremented evoked potential, an extra stimulus may be used to amplify the repolarization gradient. The amount of this amplification may depend depends on the strength and rate of the stimuli. Step 210 may be optional in some cases.

Study #1

Figure 11A:
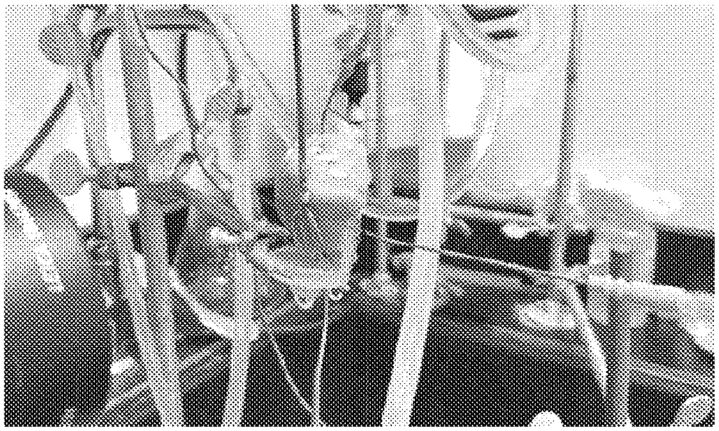
FIG. 11A shows an experimental setup for obtaining cardiac signals for an experimental study.

A study was performed to adapt a rabbit heart Langendorff optical mapping model[42] to add the recording of electrical EGMs to a commercially-available electrode array lab (Advisor HDGrid catheter, Abbott Laboratories), after its use in the clinical laboratory for animal use. This involved using a UHN research mapping system in which unipolar EGMs from a 16-electrode grid were used to record cardiac signals with a proprietary mapping system (described previously as UHN Cartesian Mapping System[43]) at a sampling rate of 1 kHz. This electrode array was chosen as spacing between the splines allowed recording of the fluorescence from the voltage-sensitive dye RH237. Fluorescence was recorded with a high-speed CMOS camera (Ultima-L, SciMedia, Costa Mesa, CA) at a rate of 500 frames/s. Spatial resolution was 160 um/pixel. A pair of twisted-pair of AWG #30 silver wires was placed in various locations on the epicardium for delivering point stimulation and evoking local wavefronts. Simultaneous optical mapping and epicardial mapping with Abbott Advisor™ HD Grid Mapping Catheter was performed in 4 rabbit Langendorff experiments. The experimental setup is shown in FIG. 11A.

For the analysis, unipolar EGMs from 4 electrodes forming a square in the middle of the grid were processed to produce a set of software-derived bipolar EGMs. The term grid refers to any regular electrode array (e.g., a 2D grid of electrodes or 3D tetrahedral arrangement of electrodes) where the inter-electrode spacing is relatively constant and known. Vectorcardiogram-like loops were derived from orthogonal sets of bipoles as described previously. A derivative of the vectorcardiogram was obtained by projecting the repolarization loop along its maximum axis where the projection may be called a loop optimized rEGM (i.e., which is a type of repolarization-optimized EGM that in this case is determined using the loop method described with respect to FIG. 5C). A measurement of repolarization duration, called $APD^v$, was measured from the onset of QRS to baseline return of the loop rEGM. It was hypothesized that rEGM provides vector-derived integrated action potential duration ($APD^v$) that correlates with local repolarization assessed by optical mapping. This was investigated to determine whether $APD^v$ may be able to better discriminate local repolarization by virtue of the loop rEGM that may resolve both the directionality problem of bipolar EGMs and far-field influencing unipolar EGMs.

For testing directionality, different wave directions were produced by varying the point-stimulation location. Repolarization duration was also modulated with the addition of pinacidil to the perfusate. The loop rEGM derived $APD^v$ measurements were compared with fluorescence signals and optical $APD_{90}$ measured from fluorescence in the middle (e.g., inner two splines of electrodes) of the 4-electrode group.

Figure 11B:
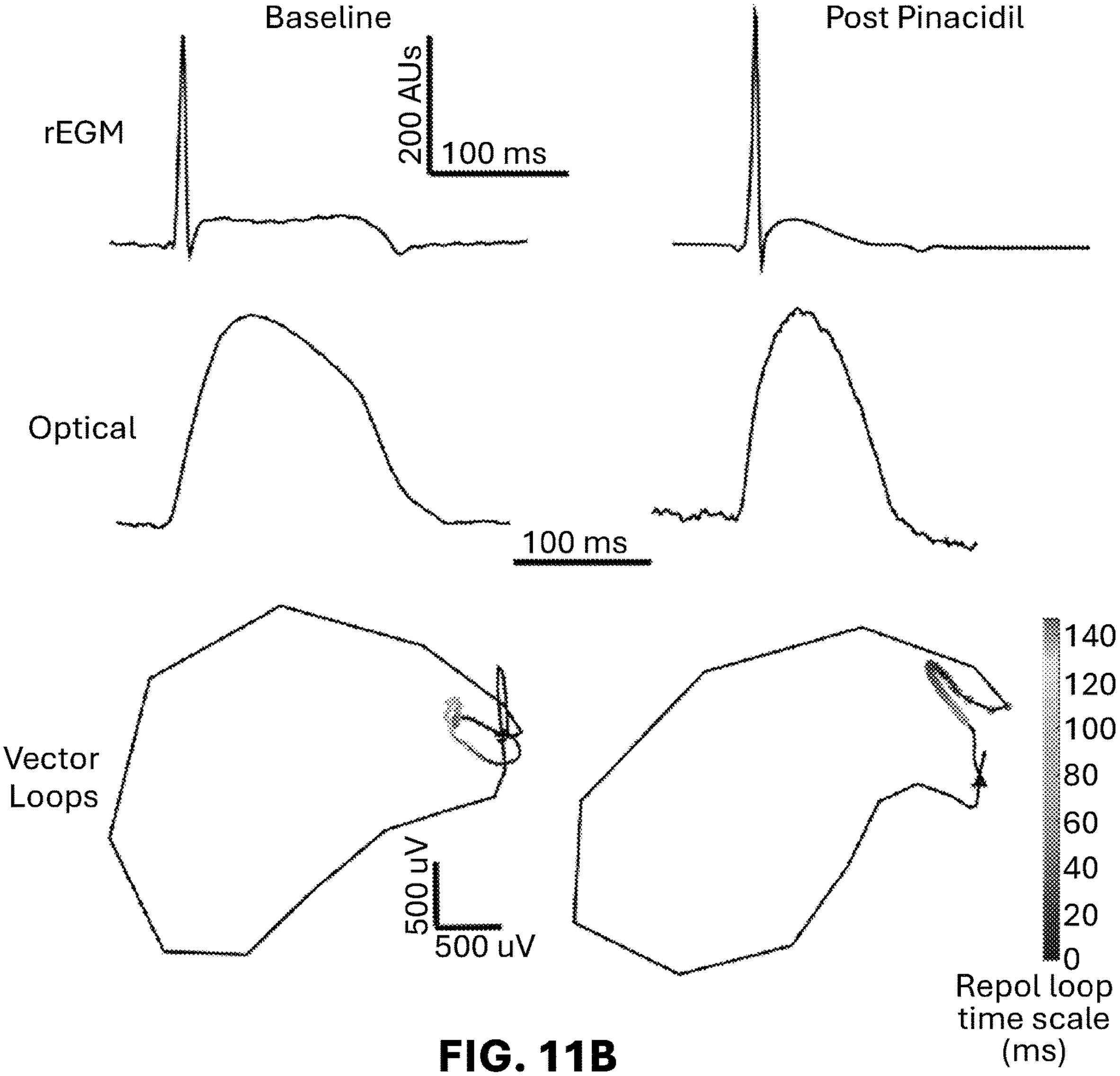
FIG. 11B shows a series of graphs (A to F) comparing signals obtained using the Langendorff optical mapping model and the orthogonal bipole loop derived rEGM method of the present teachings.

A total of 61 pairs of $APD^v$ measurements under various wavefront directions were performed. Baseline conditions showed an $APD^v$ average of 142 ms versus APD90 of 151 ms. Pinacidil was added to alter APD. After 20 uM addition of pinacidil, the ARI and APD were reduced to 68 ms and 89 ms respectively (see FIG. 11B, Panel B). Panels A and B of FIG. 11B shows examples of the rEGM signal before and after pinacidil, panels C and D of FIG. 11B show associated optical signals; and panels E and F display associated loops revealing color-coded distinct loops for the repolarization phase.

Linear correlation between $APD^v$ and APD90 showed a $R^2$ of 0.713 and a slope of 0.954. These findings suggest that multi-electrode arrays with orthogonal bipoles may provide intra-electrode cardiac vector loops that enable local APD measurements for mapping repolarization gradients. For example, both of the methods for determining rEGM described herein may be used to create 3D electro-anatomic repolarization maps to identify regions of steep repolarization gradients.

Study #2

Another study was performed to evaluate the performance of an automated repolarization technique for exploiting the unique features of equispaced electrode arrays with orthogonal bipoles—using the technique described with respect to FIG. 5B.

In this study, simultaneous optical mapping and epicardial mapping with equispaced array catheters (OPTRELL™ from Biosense and the ADVISOR™ HD grid from Abbott) was performed in 6 rabbit Langendorff experiments. Unipolar EGMs from 4 electrodes forming a square in the middle of the grid were recorded with LabChart at a sampling rate of 1000 Hz, a high pass filter setting of 0.03 Hz and a low-pass filter setting of 200 Hz. For assessment of repolarization on mapping arrays, the rEGM was created from orthogonal bipolar EGMs using the method of FIG. 5B. Optical mapping was performed with a Scimedia Ultima-L system with a sampling rate of 500 frames/s. Optical resolution was 160 um/pixel. The study involved creating epicardial waves propagating in different directions and adding Pinacidil to alter APD. $APD_{80}$ from the optical data was measured using an algorithm that provides certain parameters such as APD50 and APD80. An APD estimate from rEGM called $APD^c$ was measured from the onset of QRS to baseline return of rEGM. The rEGM derived $APD^c$ measurements were compared with fluorescence signals and optical $APD_{80}$ measured in the middle of the electrode clique. The perturbations/alternations to APD due to changing wavefronts were assessed by Optical $APD_{80}$, $APD^c$ and traditional ARI.

Figure 12B:
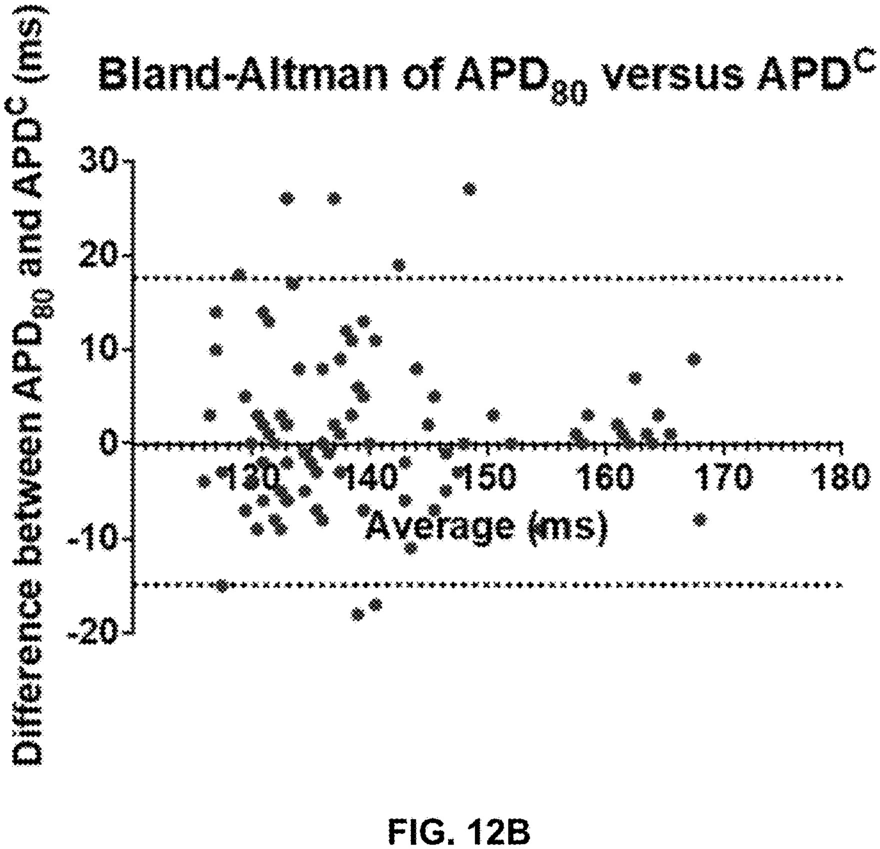
FIG. 12B shows a Bland-Altman plot comparing the gold standard $APD_{80}$ with the algorithm output, $APD^c$ for an experimental study.
Figure 12C:
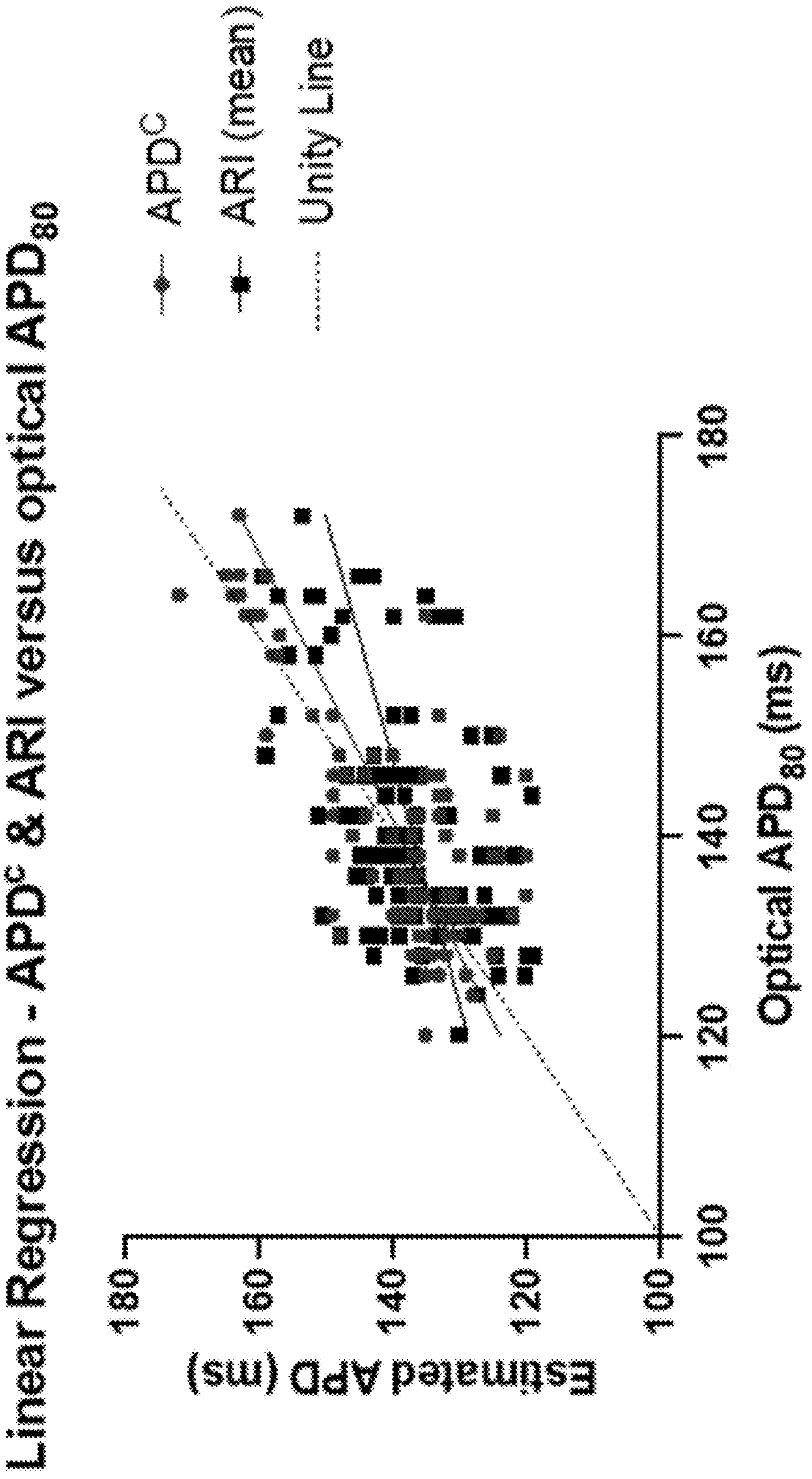
FIG. 12C shows a regression analysis of ARI and $APD^c$ compared to the optical gold standard for the experimental study data of FIG. 12B.

A comparison between $APD_{80}$ and $APD^c$ was performed from a total of 105 beats under 9 different conditions (experiments, pacing or spontaneous rhythm). FIG. 12B shows a Bland-Altman plot comparing the gold standard $APD_{80}$ with the algorithm output, $APD^v$, which was obtained based on the method shown in FIG. 5B. The Bland-Altman analysis showed a Bias of 1.362 ms between the two sets while the 95% limits of agreement were [−14.88 ms to 17.60 ms]. The graph shows that only 8 points out of 105 were outside the confidence interval. FIG. 12C shows a regression analysis of ARI and $APD^c$ compared to the optical gold standard. The regression analysis shown that the regression curve was worse for Optical $APD_{80}$ vs ARI compared to Optical $APD_{80}$ vs $APD^c$ both in terms of goodness of fit ($r^2$=0.25 versus 0.56) and in terms of slope (0.41 for ARI compared to 0.75 for $APD^c$). Accordingly, the repolarization determination method of FIG. 5B appears to be superior to the traditional unipolar ARI optical method.

Study #3

In addition to wave propagation, tissue anisotropy is thought to determine repolarization. This may explain PVC-induced vulnerability to re-entry, based on change of activation setting up arrhythmogenic repolarization gradients. However, differential repolarization effects produced by waves propagating in various directions has not been studied. Accordingly, another study was performed to determine the effect of wave direction on cardiac repolarization as measured by optical mapping and the rEGM method of FIG. 5B.

As described in the previous study, simultaneous optical mapping and epicardial mapping with equispaced array catheters (i.e., the OPTRELL™ from Biosense and the ADVISOR™ HD Grid from Abbott) was performed in 6 rabbit Langendorff experiments. Unipolar EGMs from 4 electrodes forming a square in the middle of the grid were recorded with the UHN mapping system at a sampling rate of 1000 Hz, a high pass filter setting of 0.5 Hz and a low-pass filter setting of 200 Hz. The rEGM was created from orthogonal bipolar EGMs derived from the unipolar EGMs using the technique of FIG. 5B.

Optical mapping was performed with Scimedia Ultima-L system but at a much higher sampling rate of 3333 frames/s. Epicardial waves propagating in different directions were produced by point stimulation (CL=200 ms) at various location respective to the grid array: Left (anterior LV, Pace B), right (lateral LV, Pace A), catheter distal (apex, Pace D) and catheter proximal (anterior base, Pace C). An endocardial source located transmurally across the grid was also evaluated. $APD_{80}$ from optical data was measured from using an algorithm. An APD estimate from the rEGM, called $APD^{c}$, was measured from the onset of QRS to baseline return of rEGM as described previously. The ARI were measured from the unipolar EGMs using the Wyatt method. For each method (optical, $APD^{c}$ and ARI) a statistical analysis evaluating the effect of wave propagation was performed.

Figure 13:
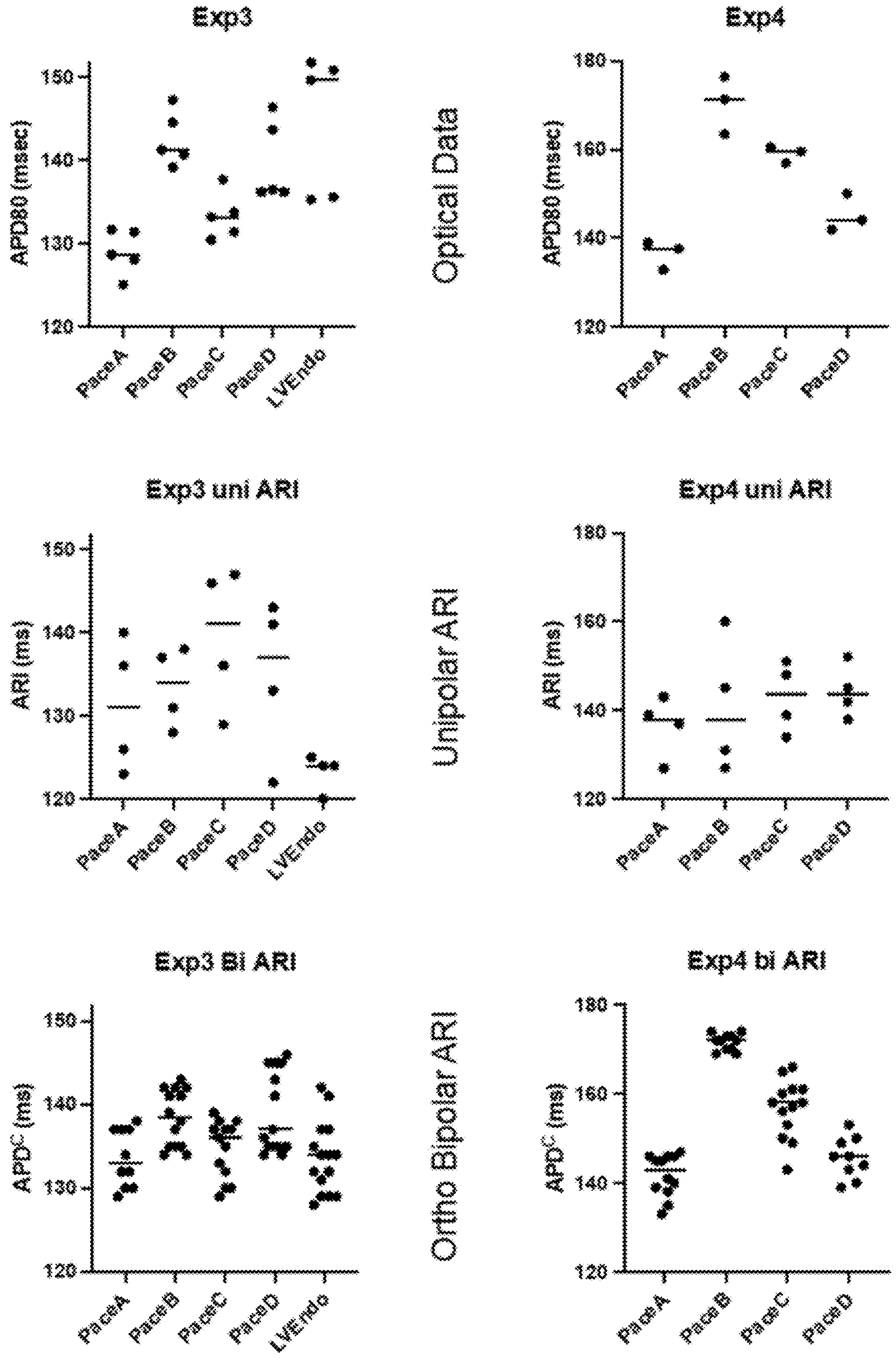
FIG. 13 illustrates study results where the graphs in the top row show the $APD_{80}$ measurements respective to wave direction for two experiments, the graphs in the middle row show ARI measurements from the two experiments, and the graphs in the last row 13 show the $APD^c$ measurements for the two experiments.

The study results are shown in FIG. 13 where the top row shows the $APD_{80}$ measurements respective to wave direction for two of the experiments. Kruskall-Wallis analysis showed a significant effect of wave direction on $APD_{80}$ ($p<0.01$ for both Experiments 3 & 4). Multiple comparisons showed a most notable effect from Pace A (lateral side). The middle row in FIG. 13 shows the ARI measurements from the same experiments. For Experiments 3 & 4, ARI failed to detect a directional repolarization difference (Exp3: $p=0.09$; Exp4: $p=0.62$). The last row in FIG. 13 shows the $APD^{c}$ measurements, which were able to successfully detect changes in wave direction (Exp3 and Exp4: $p<0.01$).

In this study it was seen that the direction of wave front propagation can change repolarization timing by as much as 30 msec. The study found that these changes were not detectable by the ARI method. However subtle changes of repolarization were successfully detected by the orthogonal bipolar EGM approach using equispaced array catheters in accordance with the teachings herein, enabling a reliable method to assess minute repolarization changes locally.

As mentioned previously, there is a need to explore alternative VT-mapping techniques beyond bipolar EGM-based depolarization abnormalities, especially in primary electrical conditions where conventional scar ablation end-points are limited or non-existent. Based on the studies reported herein, wave tail mapping has the potential to fill this void since it may be used to determine critical sites beyond what is currently understood with respect to depolarization or wavefront mapping alone. For example, ventricular repolarization assessment by mapping has a major potential adjunct role in determining critical and vulnerable VT sites and provides the impetus to develop wave tail mapping and may help improve determining targets in ischemic and non-ischemic substrate. In addition, another advantage of $APD^{c}$ is the possibility to assess local repolarization as bipolar EGMs that are less prone to far-field contamination compared to unipolar EGM-based ARI. This is clinically important as spatial repolarization gradients are considered potential sources of re-entrant ventricular tachycardias (VTs). Thus, it is important that $APD^{c}$ can detect minor changes of repolarization.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

REFERENCES

1. Auerbach D S, Grzda K R, Furspan P B, Sato P Y, Mironov S, Jalife J. Structural heterogeneity promotes triggered activity, reflection and arrhythmogenesis in cardiomyocyte monolayers. J Physiol. 2011 May 1; 589(Pt 9):2363-81.
2. Baker L C, London B, Choi B R, Salama G. Enhanced dispersion of repolarization and refractoriness in transgenic mouse hearts promotes reentrant ventricular tachycardia. Circ Res. 2000 Mar 3; 86(4):396-407.
3. Akar F G, Lauita K R, Rosenbaum D S. Cellular basis for dispersion of repolarization underlying reentrant arrhythmias. J Electrocardiol. 2000; 33 Suppl:23-31.
4. Chauhan VS, Downar E, Nanthakumar K, Parker J D, Ross H J, Chan W, et al. *Increased ventricular repolarization heterogeneity in patients with ventricular arrhythmia vulnerability and cardiomyopathy: a human in vivo study.* Am J Physiol Heart Circ Physiol. 2006 Jan; 290(1): H79-86.
5. Akar F G, Yan G X, Antzelevitvh C, Rosenbaum D S. Unique topographical distribution of M cells underlies reentrant mechanism of torsade dr pointes in the long-QT syndrome. Circulation. 2002 Mar 12; 105(10): 1247-53.
6. Banyasz T, Fulop L, Magyar J, Szentandrassy N, Varro A, Nanasi P P. Endocardial versus epicardial differences in L-type calcium current in canine ventricular myocytes studied by action potential voltage clamp. Cardiovasc Res. 2003 Apr 1; 58(1):66-75.
7. Kaufman E S, Mackall J A, Julka B, Drabek C, Rosenbaum D S. Influence of heart rate and sympathetic stimulation on arrhythmogenic T wave alternans. Am J Physiol Heart Circ Physiol. 2000 Serp;279(3): H1248-55.
8. Kuo C S, Munakata K, Reddy CP, Surawicz B. Characteristics and possible mechanism of ventricular arrhythmia dependent on the dispersion of action potential durations. Circulations 1983; 67:1356-67.
9. Cowan J C, Hilton C J, Griffiths C J, Tansuphaswadikul S Bourke J P, Murray A, et al. Sequence of epicardial repolarization and configuration of the T wave. Br Heart J. 1988 Nov; 60(5):424-433.
10. Marrus S B, Andrews C M, Cooper D H, Faddis, Rudy Y. Repolarization changes underlying long-term cardiac memory due to right ventricular pacing: noninvasive mapping with electrocardiogramaging. Cic Arrhythm Electrophysiol. 2012 Aug 1; 5(4):773-81.
11. Rivaud M R, Bayer J D, Cluitmans M, van der Waal J, Bear L R, Boukens B J, et al. Critical repolarization gradients determine the induction of reentry-based torsades de pointes arrhythmia models of long QT syndrome. Heart Rhythm. 2021 Feb; 18(2):278-287.
12. Haissaguerre M, Nademanee K, Sacher F, Cheniti G, Hocini M, Surget E, et al. Multisite conduction block in the epicardial substrate of Brugada syndrome. Heart Rhythm. 2022 Mar; 19(3):417-426.
13. Behr E R, Ben-Haim Y, Ackerman M J, Krahn A D, Wilde A A M. Brugada syndrome and reduced right ventricular outflow tract conduction reserve: a final common pathway? Eur Heart J. 2021 Mar 14; 42(11): 1073-1081.
14. Nademanee K, Veerakul G, Nogami A, Lou Q, Hocini M, Coronel, et al. Mechanism of the effects of sodium channel blockade on arrhythmogenic substrate in Brugada syndrome. Heart Rhythm. 2022 Mar; 19(3):407-416.
15. Bhar-Amato J, Finlay M, Santos D, Orini M, Chaubey S, Vyas V, et al. Pharmacological Modulation of Right Ventricular Endocardial-Epicardial Gradients in Brugada Syndrome. Circ Arrhythm Electrophysiol. 2018 Sep; 11(9): e006330.
16. Nademanee K, Raju H, de Noronha S V, Papadakis M, Robinson L, Rothery S, et al. Fibrosis, Connexin-43, and Conduction Abnormalities in the Bruguda Syndrome. J Am Coll Cardiol. 2015 Nov 3; 66(18): 1976-1986.
17. Szel T, Antzelevitch C. Abnormal repolarization as the basis for late potentials and fractionated electrograms recorded from epicardium in experimental models of Brugada syndrome. J Am Coll Cardiol. 2014 May 20; 63(19):2037-45.
18. Patocskai B, Yoon N, Antzelevitch C. Mechanisms Underlying Epicardial Radiofrequency Ablation to Suppress Arrhythmogenesis in Experimental Models of Brugada Syndrome. JACC Clin Electrophysiol. 2017 Apr; 3(4):353-363.
19. Engelman Z J, Trew M L, Smaill B H. Structural heterogeneity alone is a sufficient substrate for dynamic instability and altered restitution. Circ Arrhythm Electrophysiol. 2010 Apr; 3(2):195-203.
20. Nademanee K and Wilde A A M. Repolarization Versus Depolarization Defects in Brugada Syndrome: A Tale of 2 Different Electrophysiologic Settings? JACC Clin Electrophysiol. 2017 Apr; 3(4):364-366.
21. Kubala M, Xie S, Santangeli P, Garcia F, Supple G E, Schaller R D, et al. Analysis of local ventricular repolarization using unipolar recordings in patients with arrhythmogenic right ventricular cardiomyopathy. J Interv Card Electrophysiol. 2020 Mar; 57(2):261-270.
22. Antzelevitch C, Fish J. Electrical heterogeneity within the ventricular wall. Basic Res Cardiol. 2001; 96(6): 517-27.
23. Downar E, Janse MJ, Bhaskaran A, Niri A, Vellup-pillai A, Masse S, et al. High density intramural mapping of post-infarct premature ventricular contractions and ventricular tachycardia. Pacing Clin Electrophysiol. 2021 Oct; 44(10):1781-1785.
24. Nair K, Farid T, Selvaraj R, Umapathy K, Masse S, Sevaptsidis et al. Searching for functional M cells in the intact whole human heart: Insights from human langendorff mapping. Canadian Journal of Cardiology. 2011 27(5), S314.
25. Srinivasan N T, Orini M, Providencia R, Dhinoja M B, Lowe MD, Ahsan S Y, et al. Prolonged action potential duration and dynamic transmural action potential duration heterogeneity underlie vulnerability to ventricular tachycardia in patients undergoing ventricular tachycardia ablation. Europace. 2019; 21:616-625
26. Peters N S, Green C R, Poole-Wilson P A, Severs N J. Reduced content of connexin43 gap junctions in ventricular myocardium from hypertrophied and ischemic human hearts. Circulation 1993; 88:864-75.
27. Srinivasan N T, Garcia J, Schilling R J, Ahsan S, Hunter R J, Lowe M, et al. Dynamic spatial dispersion of repolarization is present in regions critical for ischemic ventricular tachycardia ablation. Heart rhythm 02. 2021; 2:280-289.
28. Callans D J, Donahue J K. Repolarization Heterogeneity in Human Post-Infarct Ventricular Tachycardia. J Am Coll Cardiol EP. 2022 Jun, 8(6):713-718.
29. Millar C K, Kralios F A, Lux R L. Correlation between refractory periods and activation-recovery intervals from electrograms: effects of rate and adrenergic interventions. Circulation. 1985:72:1372-1379.
30. Anter E, Kleber A G, Rottmann M, Leshem E, Barkagan M, Tschabrunn C M, et al. Infarct-Related Ventricular Tachycardia: Redefining the Electrophysiological Substrate of the Isthmus During Sinus Rhythm. JACC Clin Electrophysiol. 2018; 4(8): 1033-48.
31. Kelemen K, Greener I D, Wan X, Parajuli S, Donahue J K. Heterogeneous repolarization creates ventricular tachycardia circuits in healed myocardial infarction scar. Nat Commun. 2022; 13:830.
32. Orini M, Graham A J, Srinivasan N T, Campos F O, Hanson B M, Chow A, et al. Evaluation of the reentry vulnerability index to predict ventricular tachycardia circuits using high-density contact mapping. Hear Rhythm. 2020 Apr; 14(4):576-583
33. Martin C A, Orini M, Srinivasan N T, Bhar-Amato J, Honarbakhsh S, Chow A W, et al. Assessment of a conduction-repolarisation metric to predict Arrhythmogenesis in right ventricular disorders. Int J Cardiol. 2018 Nov; 271:75-80.
34. Salama G. Optical measurements of transmembrane potential in heart. In: Loew L, ed. Spectroscopic Probes of Membrane Potential. New York, NY: CRS Uniscience; 1988; 3:137-199.
35. Kanai A, Salama. Optical mapping reveals that repolarization spreads anisotropically and is guided by fiber orientation in guinea pig hearts. Circ Res. 1995 Oct; 77(4):784-802.
36. Joyncr R W. Modulation of repolarization by electrotonic interactions. Jpn Heart J. 1986; 27:167-183
37. Lesh M D, Pring M, Spear J F. Cellular uncoupling can unmask dispersion of action potential duration in ventricular myocardium: a computer modelling study. Circ Res. 1989; 65:1426-1440.
38. Graham A J, Orini M, Zacur E, Dhillion G, Daw H, Srinivasan N T, et al. Simultaneous Comparison of Electrocardiogramaging and Epicardial Contact Mapping in Structural Heart Disease. Circ Arrhythm Electrophysiol.2019 Apr; 12(4)e007120.
39. Ramanathan C, Ghanem R N, Jia P, Ryu K, Rudy Y. Noninvasive electrocardiogramaging for cardiac electrophysiology and arrhythmia. Nat Med. 2004 Apr; 10(4):422-8.
40. Lambiase P D. Rediscovering Repolarization: Timing is Everything. JACC Clin Electrophysiol. 2022 Jun; 8(6):719-721.
41. Masse S, Niri A, Asta J, Azam M A, Lai P F H, Magtibay K, et al. Electro-anatomic repolarization mapping with orthogonal bipoles and multi-electrode arrays: The next frontier in catheter technology. Heart Rhythm. 2022 May; 19(5): S9-S10.

42. Azam M A, Zamiri N, Massé S, Kusha M, Lai P F H, Nair G K, et al. Effects of Late Sodium Current Blockade on Ventricular Refibrillation in a Rabbit Model. Circ Arrhythm Electrophysiol. 2017 Mar; 10(3): e004331.

43. Masse S, Downar E, Chauhan V, Sevaptsidis E, Nanthakumar N. Ventricular fibrillation in myopathic human hearts: mechanistic insights from in vivo global endocardial and epicardial mapping. *Am J Physiol Heart Circ Physiol.* 2007; 292:H2589-97.

The invention claimed is:

1. A method for determining at least one repolarization value from Electrogram (EGM) data obtained from a heart using an electrode array, wherein the method is performed by at least one processor and/or circuitry wherein the method comprises:

obtaining bipolar EGM data from the EGM data obtained from the heart by subtracting EGM data for a first electrode from EGM data for a second electrode where the first and second electrodes are adjacent to one another in the electrode array;

determining at least one orthogonal bipolar compound electrogram from the bipolar EGM data by:

obtaining an Along Bipolar EGM for a first pair of electrodes disposed adjacent to one another and along a linear array of electrodes from the electrode array;

obtaining an Across Bipolar EGM for a second pair of electrodes that are orthogonal to the first pair of electrodes and share a common electrode therewith; and combining the Along Bipolar EGM and the Across Bipolar EGM in an orthogonal manner to obtain the at least one orthogonal bipolar compound electrogram; and determining the at least one repolarization value from the at least one orthogonal bipolar compound electrogram.

2. The method according to claim 1, wherein the method further comprises filtering the EGM data by performing high pass filtering using a cutoff frequency of about 0.02 Hz or about 0.05 Hz.

3. The method according to claim 1, wherein the method comprises preprocessing the obtained EGM data by performing baseline correction and/or noise reduction.

4. The method according to claim 1, wherein the method comprises obtaining the bipolar EGM data by applying differential amplification when obtaining the EGM data from the heart.

5. The method according to claim 1, wherein the method comprises obtaining the bipolar EGM data from a principal component referenced unipole or an EGM derived from a Laplacian operation.

6. The method according to claim 1, wherein combining the Along Bipolar EGM and the Across Bipolar EGM comprises squaring the Along Bipolar EGM, squaring the Across Bipolar EGM and adding the squared Along Bipolar EGM and squared Across Bipolar EGM.

7. The method according to claim 1, wherein the at least one repolarization value is obtained by:

determining a local activation time;

determining a fiducial time point based on an intersection of a first line that is aligned with a diastolic baseline and a second that is aligned with a most negative slope of a portion of the at least one orthogonal bipolar compound EGM; and obtaining the at least one repolarization value from a repolarization time defined by a time duration between the local activation time and the fiducial time point.

8. The method according to claim 1, wherein the method comprises obtaining a plurality of repolarization values corresponding to various locations on an electrode grid defined by the electrode array.

9. The method according to claim 8, wherein the method further comprises determining the plurality of repolarization values for generating a repolarization map that is displayed on a display, stored in a data store, transmitted to another computing device or any combination thereof.

10. The method according to claim 9, wherein the repolarization map is used to guide a cardiac procedure including catheter ablation and/or tissue debulking.

11. A non-transitory computer readable medium storing program instructions that when executed by a processor cause the processor to perform a method for determining at least one repolarization value where the method is defined according to claim 1.

12. A system for determining at least one repolarization value from Electrogram (EGM) data obtained from a heart, wherein the system comprises:

an electrode array for obtaining EGM data from the heart;

an instrumentation unit that is coupled to the electrode array and comprises circuitry that is configured to receive and preprocess the obtained EGM data;

memory for storing program instructions; and at least one processor that is coupled to the memory and the instrumentation unit, wherein when the at least one processor executes the program instructions, the at least one processor is configured to perform a method that is defined according to claim 1.

13. The system of claim 12, wherein the instrumentation unit comprises at least one filter for filtering the EGM data by performing high pass filtering using a cutoff frequency of about 0.02 Hz or about 0.05 Hz.

14. The system of claim 12, wherein the circuitry of the instrumentation unit and/or the at least one processor is configured to: (a) preprocess the obtained EGM data by performing baseline correction and/or (b) preprocess the obtained EGM data by performing noise reduction.

15. The system of claim 12, wherein the instrumentation unit comprises at least one differential amplifier for obtaining the bipolar EGM data by applying differential amplification when obtaining the EGM data from the heart.

16. The system of claim 12, wherein the at least one processor is configured to obtain the bipolar EGM data from a principal component referenced unipole or is an EGM derived from a Laplacian operation.

17. The system of claim 12, wherein the circuitry of the instrumentation unit and/or the at least one processor is configured to obtain the bipolar EGM data by subtracting EGM data for a first electrode from EGM data for a second electrode where the first and second electrodes are adjacent to one another in the electrode array.

18. The system of claim 12, wherein the at least one processor is configured to combine the Along Bipolar EGM and the Across Bipolar EGM by squaring the Along Bipolar EGM, squaring the Across Bipolar EGM and adding the squared Along Bipolar EGM and squared Across Bipolar EGM.

19. The system of claim 12, wherein the at least one processor is configured to obtain the at least one repolarization value for a given orthogonal bipolar compound electrogram by: determining a local activation time;

determining a fiducial time point based on an intersection of a first line that is aligned with a diastolic baseline and a second that is aligned with a most negative slope of a portion of the given orthogonal bipolar compound EGM; and obtaining the at least one repolarization value from a repolarization time defined by a time duration between the local activation time and the fiducial time point.

20. The system of claim 12, wherein the at least one processor is configured to: (a) obtain a plurality of repolarization values corresponding to various locations on an electrode grid defined by the electrode array; and/or (b) determine a plurality of repolarization values for generating a repolarization map that is displayed on a display, stored in a data store, transmitted to another computing device or any combination thereof.

21. A method for determining at least one repolarization value from Electrogram (EGM) data obtained from a heart using an electrode array, wherein the method is performed by at least one processor and/or circuitry wherein the method comprises:

obtaining bipolar EGM data from the EGM data obtained from the heart by subtracting EGM data for a first electrode from EGM data for a second electrode where the first and second electrodes are adjacent to one another in the electrode array;

determining at least one loop vector compound electrogram from the bipolar EGM data by:

selecting an orthogonal set of electrodes where horizontally adjacent electrodes are on separate linear electrode arrays and vertically horizontal adjacent electrodes are on a same linear electrode array;

forming an orthogonal set of bipoles using the selected orthogonal set of electrodes;

deriving a vectorcardiogram-like loop from the orthogonal set of bipoles;

identifying a T loop portion from the vectorcardiogram-like loop; and obtaining a derivative of the vectorcardiogram-like loop by obtaining a time projection of the T loop portion along a maximum axis of the T loop portion thereby forming the at least one loop vector compound electrogram; and determining the at least one repolarization value from the at least one loop vector compound electrogram.

22. The method according to claim 21, wherein the at least one repolarization value is obtained by:

determining a first time point that is an onset of a QRS complex in the at least one loop vector compound electrogram;

determining a second time point that is a baseline return of the at least one loop vector compound electrogram; and obtaining the at least one repolarization value from a repolarization time defined by a time duration between the first time point and the second time point.

23. A system for determining at least one repolarization value from Electrogram (EGM) data obtained from a heart, wherein the system comprises:

an electrode array for obtaining EGM data from the heart;

an instrumentation unit that is coupled to the electrode array and comprises circuitry that is configured to receive and preprocess the obtained EGM data;

memory for storing program instructions; and at least one processor that is coupled to the memory and the instrumentation unit, wherein when the at least one processor executes the program instructions, wherein the at least one processor is configured to obtain at least one given loop vector compound electrogram by: selecting an orthogonal set of electrodes where horizontally adjacent electrodes are on separate linear electrode arrays and vertically horizontal adjacent electrodes are on a same linear electrode array: form an orthogonal set of bipoles using the selected orthogonal set of electrodes; derive a vectorcardiogram-like loop from the orthogonal set of bipoles; identifying a T loop portion from the vectorcardiogram-like loop; and obtain a derivative of the vectorcardiogram-like loop by obtaining a time projection of the T loop portion along a maximum axis of the T loop portion thereby forming the at least one loop vector compound electrogram; and determining the at least one repolarization value from the at least one loop vector compound electrogram.

24. The system of claim 23, wherein the at least one processor is configured to obtain the at least one repolarization value for at least one loop vector compound electrogram by: determining a first time point that is an onset of a QRS complex in the at least one loop vector compound electrogram; determining a second time point that is a baseline return of the at least one loop vector compound electrogram; and obtaining the at least one repolarization value from a repolarization time defined by a time duration between the first time point and the second time point.

* * * * *